US007648982B2

(12) United States Patent
Shafer et al.

(10) Patent No.: US 7,648,982 B2
(45) Date of Patent: *Jan. 19, 2010

(54) OPIOID DELIVERY SYSTEM

(75) Inventors: Steven Louis Shafer, Mountain View, CA (US); Orlando Ricardo Hung, Halifax (CA); Diana Helen Pliura, Mississauga (CA)

(73) Assignee: YM Biosciences Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/927,145

(22) Filed: Aug. 27, 2004

(65) Prior Publication Data

US 2005/0084523 A1 Apr. 21, 2005

Related U.S. Application Data

(63) Continuation-in-part of application No. 10/788,466, filed on Mar. 1, 2004.

(60) Provisional application No. 60/450,333, filed on Feb. 28, 2003.

(51) Int. Cl.
*A61K 9/127* (2006.01)
*A61K 9/12* (2006.01)
*A61K 31/445* (2006.01)
*A61K 31/4468* (2006.01)
*A61M 15/00* (2006.01)
*A61M 13/00* (2006.01)

(52) U.S. Cl. ............... 514/225.5; 424/450; 128/202.17; 128/203.15; 128/200.14

(58) Field of Classification Search .................. 424/43, 424/45, 417, 450
See application file for complete search history.

(56) References Cited

U.S. PATENT DOCUMENTS

| | | | |
|---|---|---|---|
| 4,885,173 | A | 12/1989 | Stanley et al. |
| 5,288,498 | A * | 2/1994 | Stanley et al. ............... 424/440 |
| 5,451,408 | A | 9/1995 | Mezei et al. |
| 5,507,277 | A | 4/1996 | Rubsamen et al. |
| 5,694,919 | A | 12/1997 | Rubsamen et al. |
| 5,724,957 | A | 3/1998 | Rubsamen et al. |
| 5,735,263 | A | 4/1998 | Rubsamen et al. |
| 5,910,301 | A | 6/1999 | Farr et al. |
| 6,024,090 | A | 2/2000 | Gonda et al. |
| 6,098,620 | A | 8/2000 | Lloyd et al. |
| 6,264,981 | B1 | 7/2001 | Zhang et al. |
| RE38,407 | E | 1/2004 | Mezel et al. |
| 2001/0007665 | A1 | 7/2001 | Illum et al. |
| 2002/0044966 | A1 | 4/2002 | Bartholomaeus et al. |
| 2002/0058050 | A1 | 5/2002 | Sackler et al. |
| 2003/0015197 | A1 | 1/2003 | Hale et al. |
| 2003/0017119 | A1 | 1/2003 | Rabinowitz et al. |
| 2003/0035837 | A1 | 2/2003 | Sackler et al. |
| 2003/0092701 | A1 | 5/2003 | Lalley |
| 2003/0157162 | A1 * | 8/2003 | Krugner-Higby et al. ... 424/450 |
| 2004/0024006 | A1 | 2/2004 | Simon |

FOREIGN PATENT DOCUMENTS

| | | |
|---|---|---|
| CA | 2119976 | 9/1995 |
| CA | 2446916 | 11/2002 |
| WO | WO 90/07333 | 7/1990 |

OTHER PUBLICATIONS

Hung, O. R. et al. "Pharmacokinetics of Inhaled Liposome Encapsulated Fentanyl," Anesthesiology, 1995, 83(2), 277-284.*
Tan, S. et al. "Sustained Tissue Drug Concentrations Following Inhalation of Liposome-Encapsulated Fentanyl in Rabbits," Drug Delivery, 1996, 3(4), pp. 251-254.*
Drug Information Handbook, Lexi-Comp, Inc.: Hudson, OH, 1999-2000, pp. 37-39, 414-416, 651-652, and 1099-1100.*
Lötsch, J., "Pharmacokinetic-Pharmacodynamic Modeling of Opioids," Journal of Pain and Symptom Management, May 2005, 29 (5S), pp. S90-S103.*
Dershwitz et al. "Pharmacokinetics and pharmacodynamics of inhaled versus intravenous morphine in healthy volunteers," Anesthesiology, 2000, 93(3), pp. 619-628 (Abstract Only).*
Shafer et al. "Pharmacokinetics, Pharmacodynamics, and Rational Opioid Selection," Anesthesiology, 1991, 74(1), pp. 53-63 (Abstract Only).*
"A Model of the Ventilatory Depressant Potency of Remifentanil in the Non-steady State" (2003), vol. 99, No. 4, Anesthesiology, pp. 779-787.
Orlando R. Hung, "Sustained Analgesic Effect of Aerosolized Liposome-Encapsulated Fentanyl".
Jaffe AB et al. Rats self-administer sufentanil in aerosol form. Psychopharmacology (Berl). 1989; 99(3): 289-93.
Higgins MJ et al. Inhaled nebulised fentanyl for postoperative analgesia. Anaesthesia. Nov. 1991; 46(11): 973-6.
Mather LE et al. Pulmonary administration of aerosolised fentanyl: pharmacokinetic analysis of systemic delivery. Br J Clin Pharmacol. Jul. 1998; 46(1): 37-43.

* cited by examiner

*Primary Examiner*—Ernst V Arnold
*Assistant Examiner*—James Henry Alstrum-Acevedo
(74) *Attorney, Agent, or Firm*—Ridout + Maybee LLP; Charles A. Boulakia

(57) ABSTRACT

An opioid formulation for pulmonary administration in the treatment or management of pain, a pulmonary drug delivery device containing, method of administering, kit containing, and uses of same. The formulation contains at least one rapid-onset opioid and preferably also contains a sustained-effect opioid to reduce the frequency of administration. The invention employs the side effects of the opioid formulation to permit patients to self-limit drug intake, thereby avoiding toxicity while achieving analgesia. A pharmacokinetic and pharmacodynamic model is employed to determine optimum drug formulations and optimum parameters for administration.

16 Claims, 27 Drawing Sheets

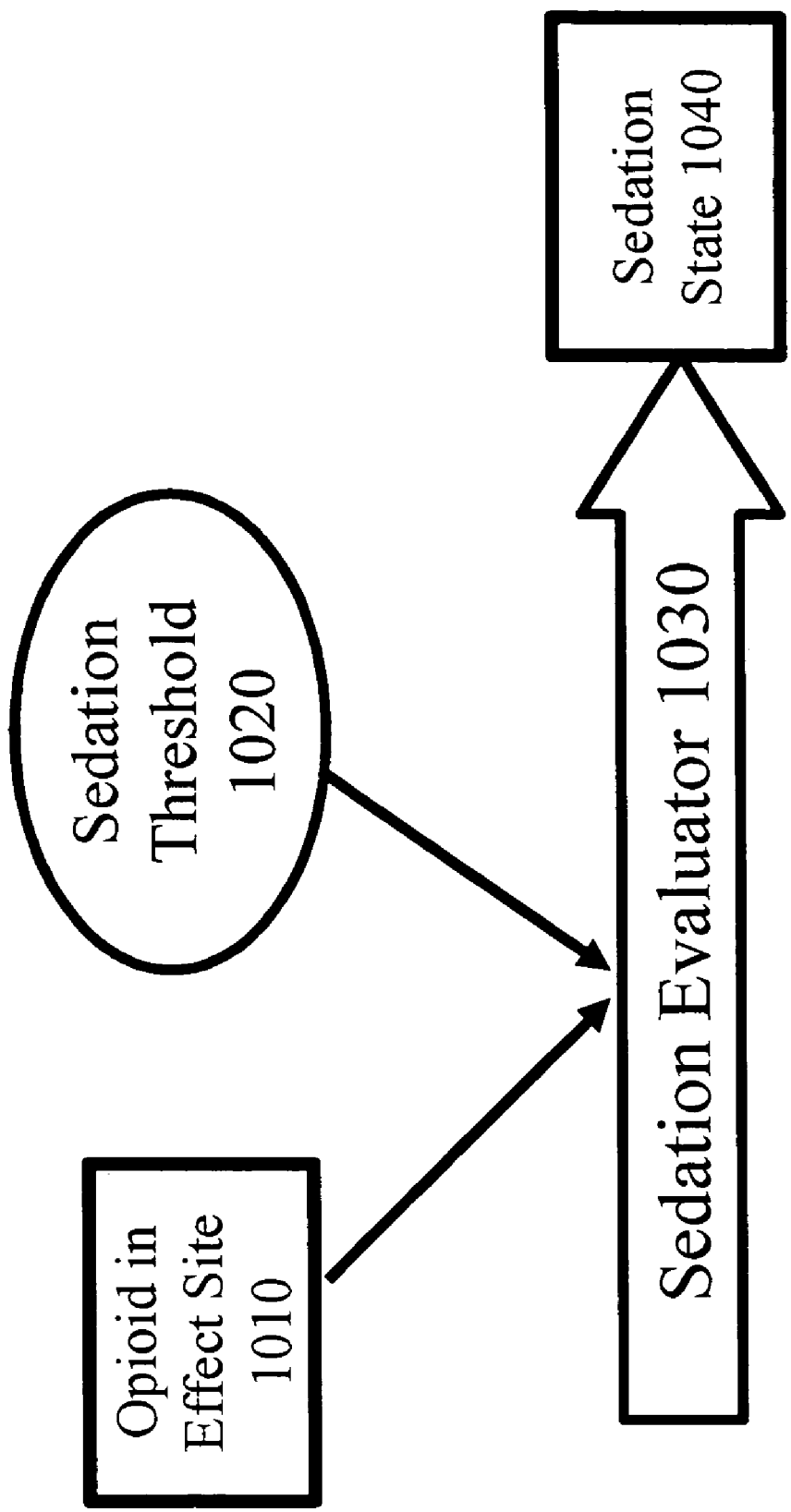

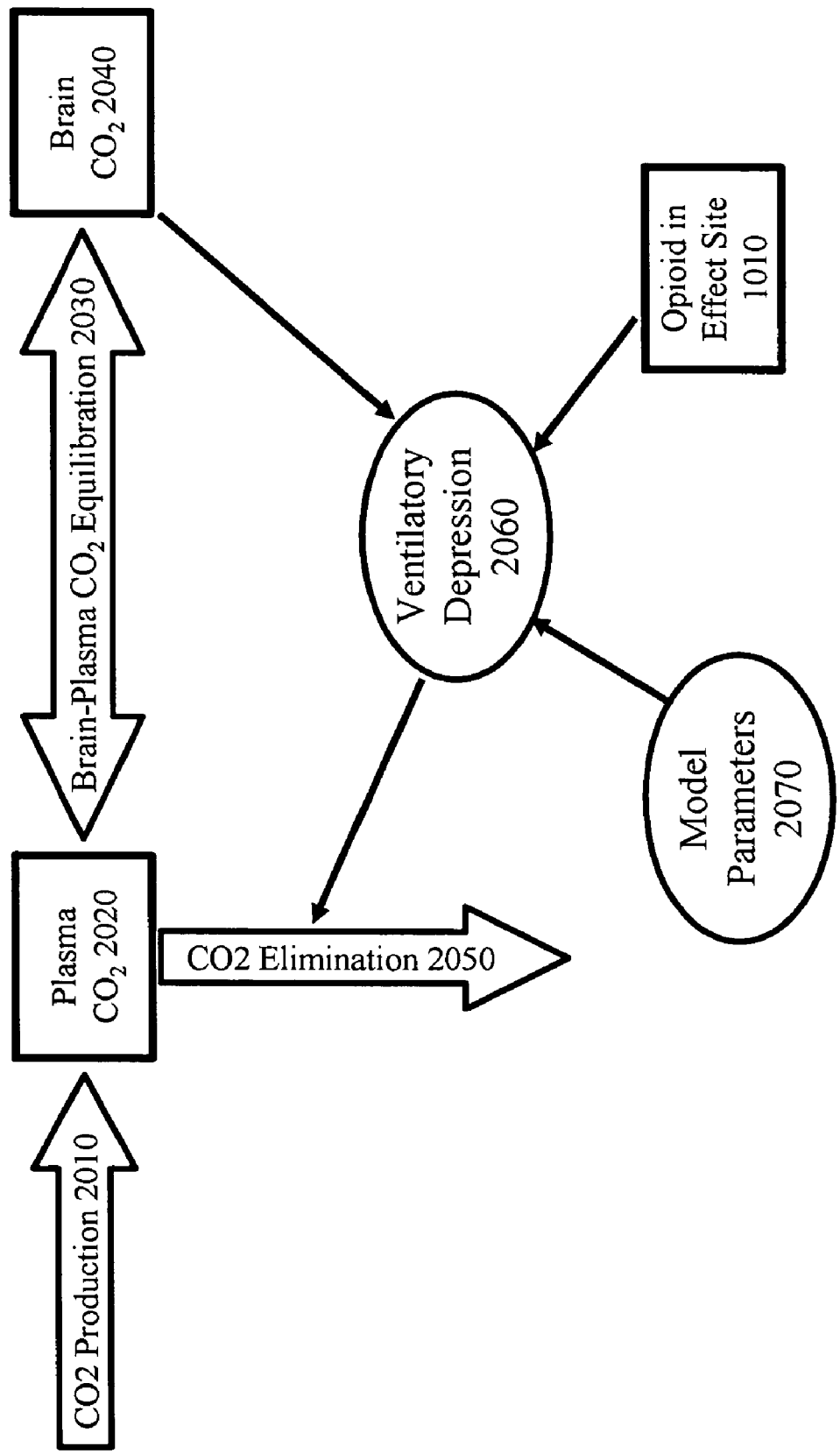
Figure 2: Ventilatory Depression Model

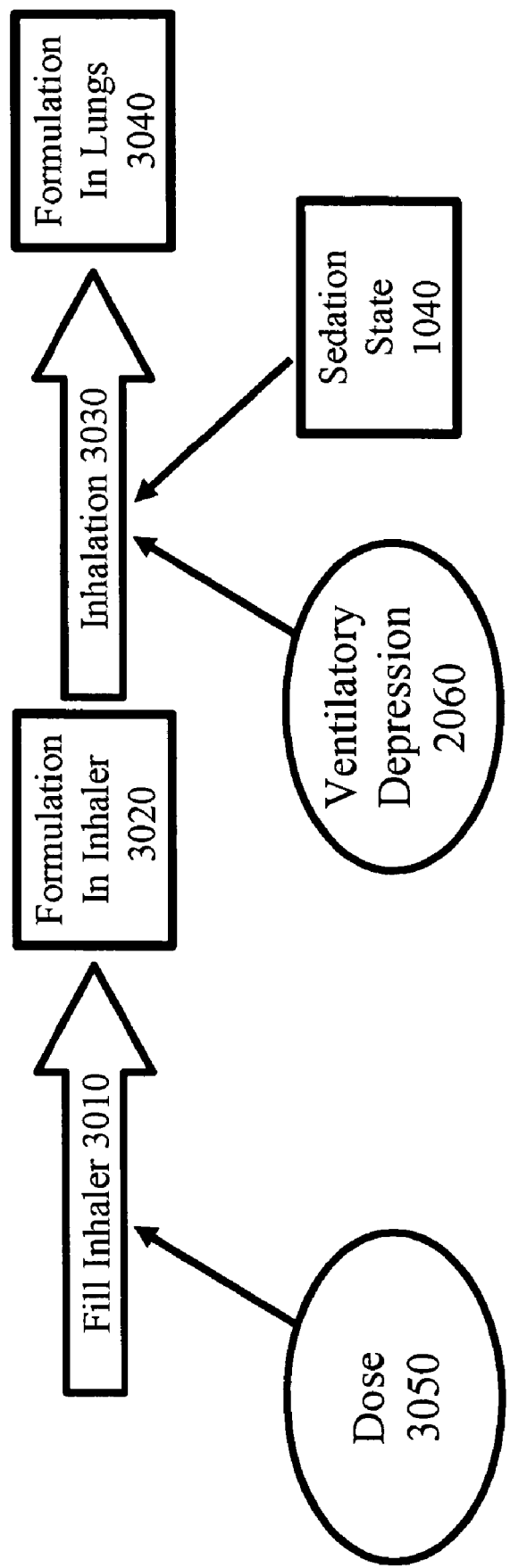

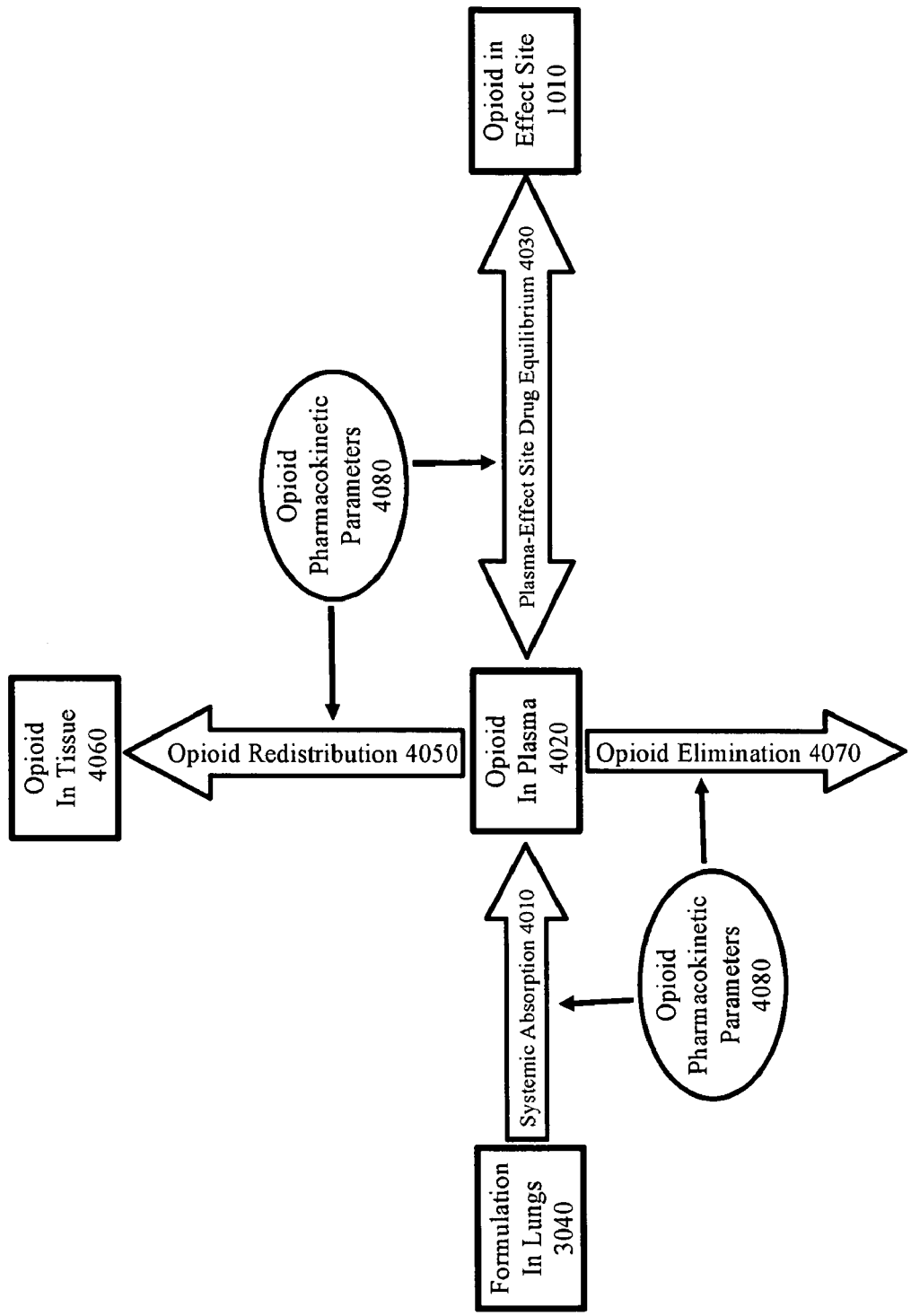
Figure 4: Pharmacokinetic Model

Figure 5A
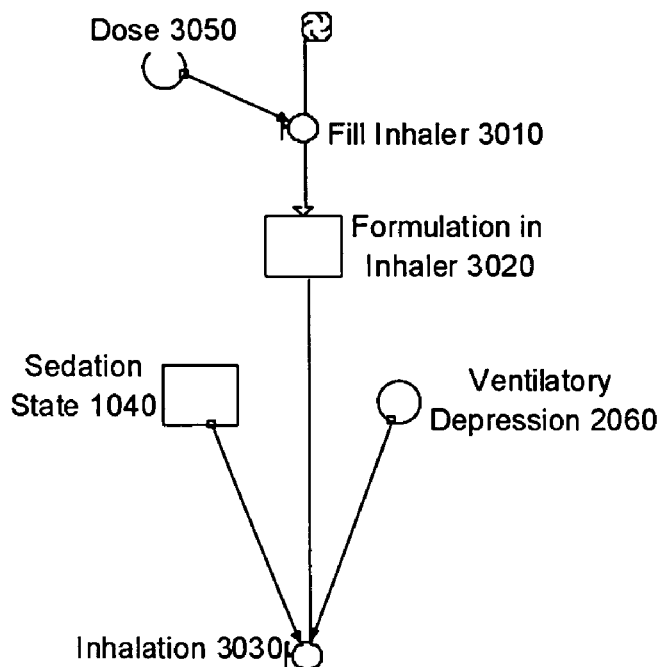
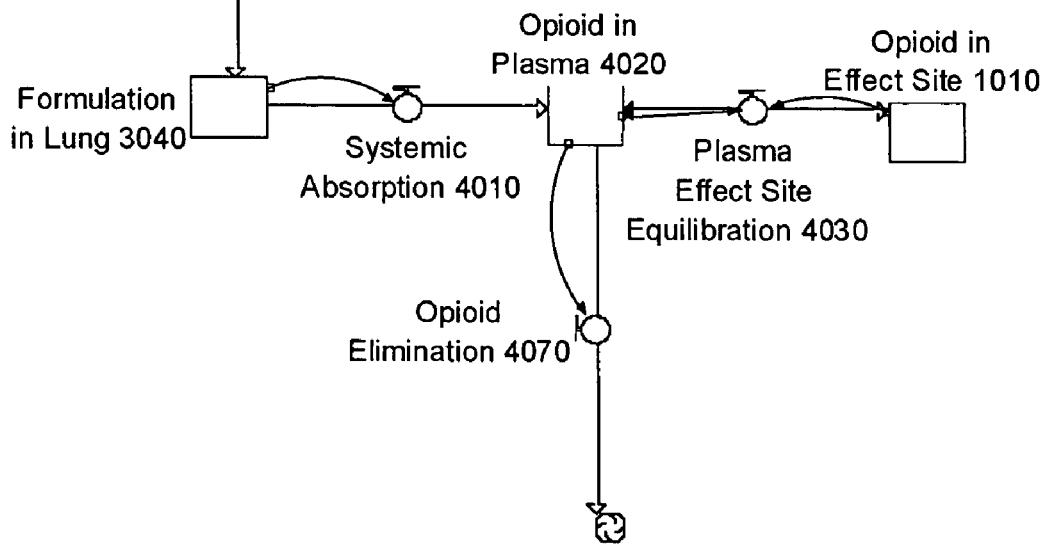

Figure 5B
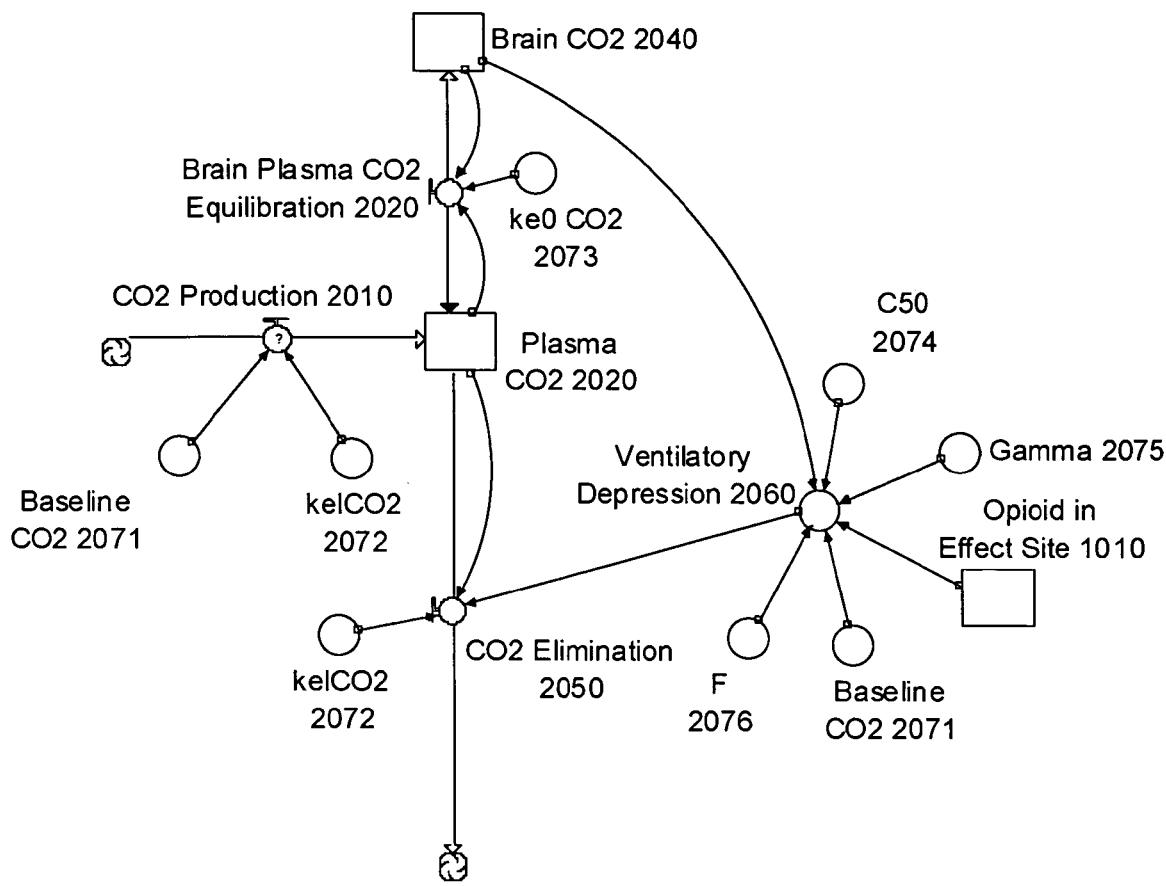
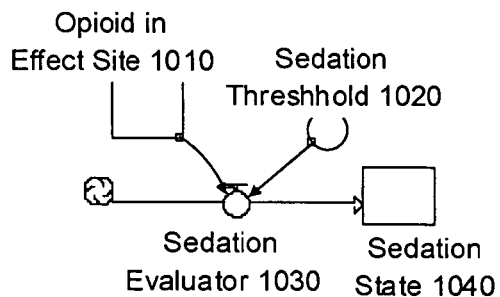

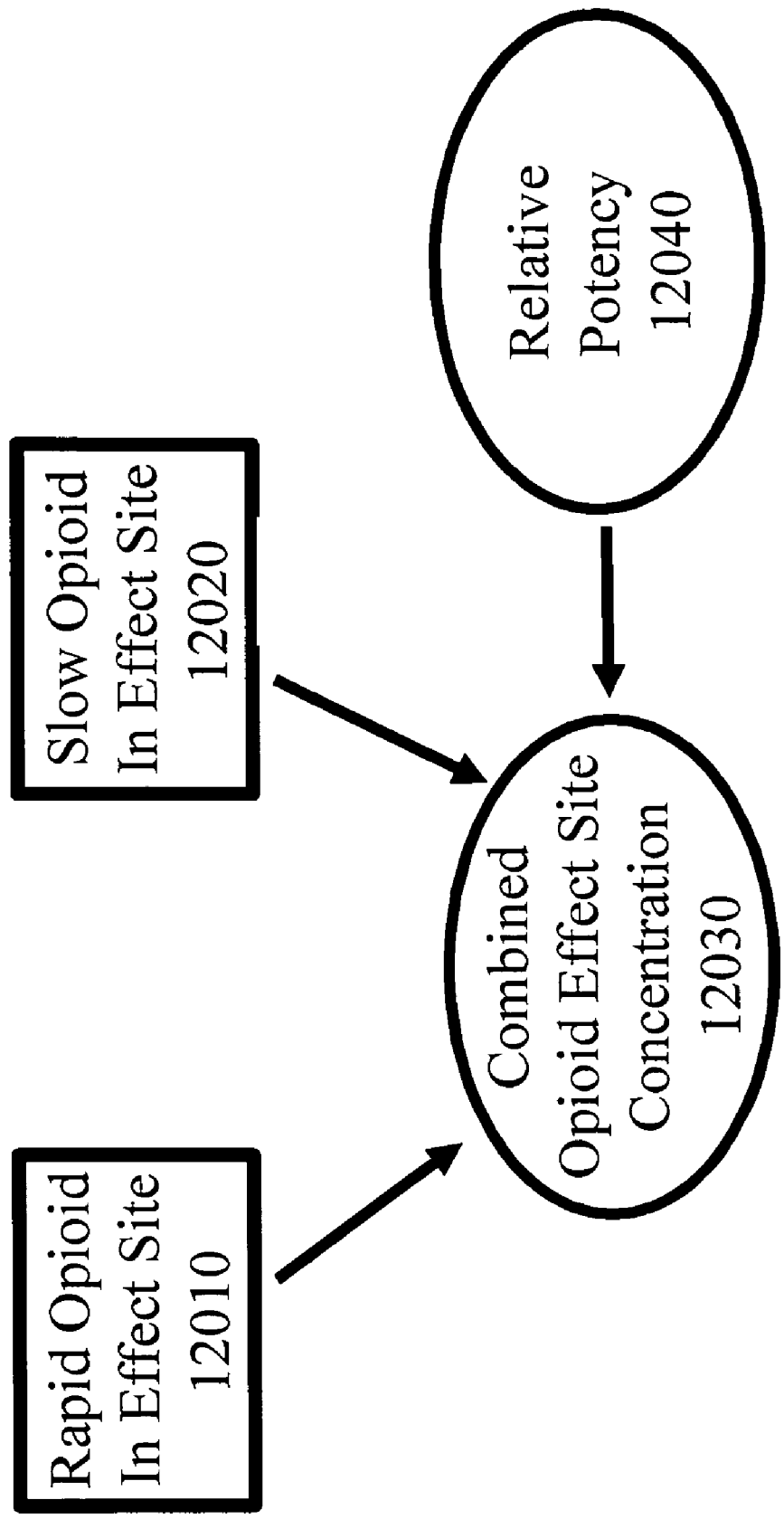
Figure 12: Two Opioid Model

Figure 13A: The elements of the invention, wherein two opioids are administered through inhalation.
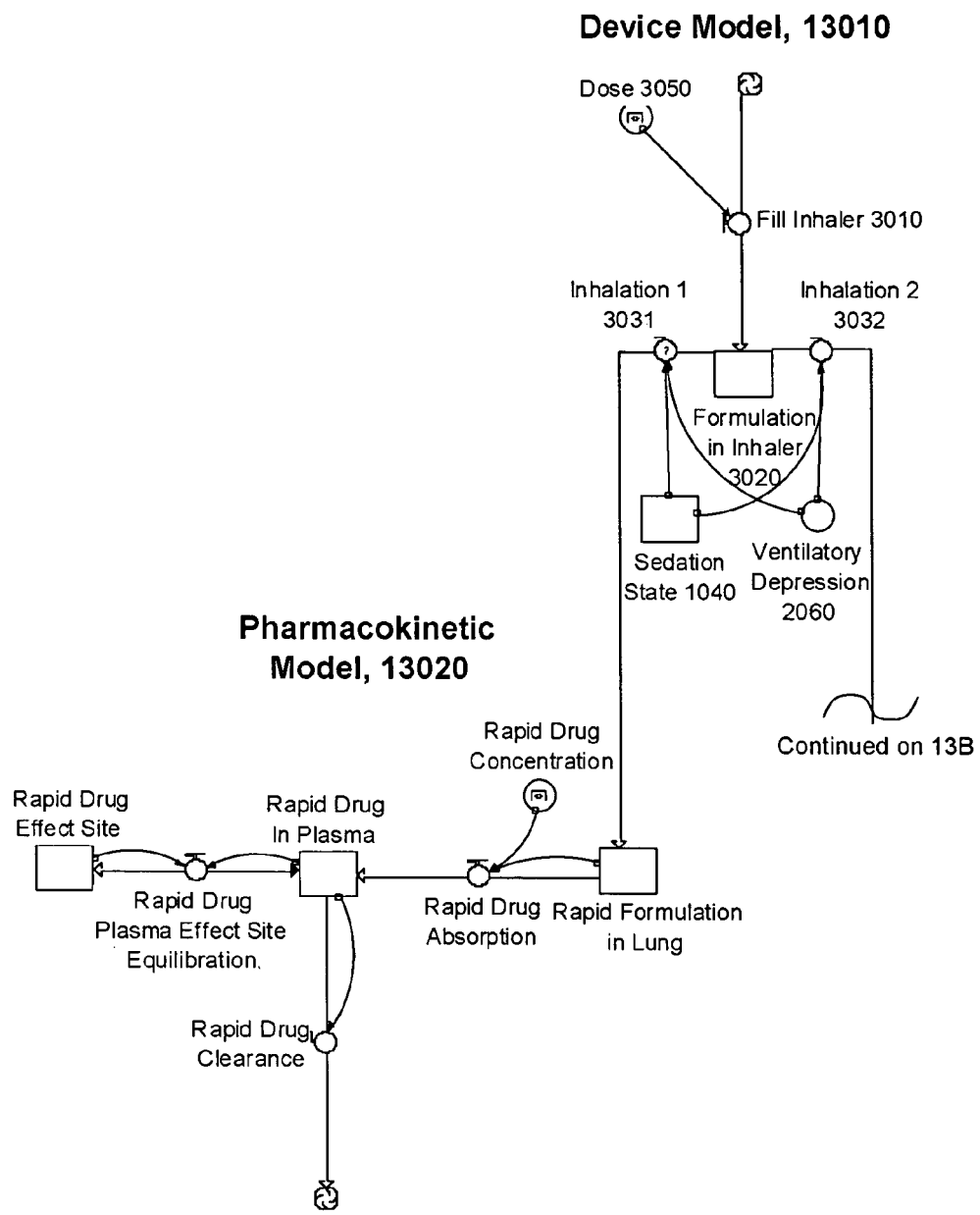

Figure 13B The elements of the invention, wherein two opioids are administered through inhalation.
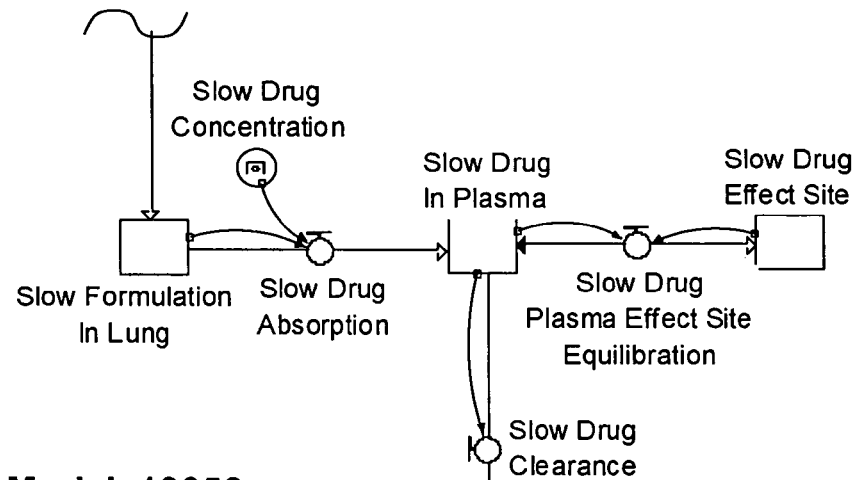
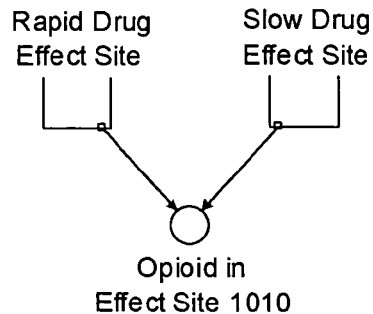

Figure 13C The elements of the invention, wherein two opioids are administered through inhalation.
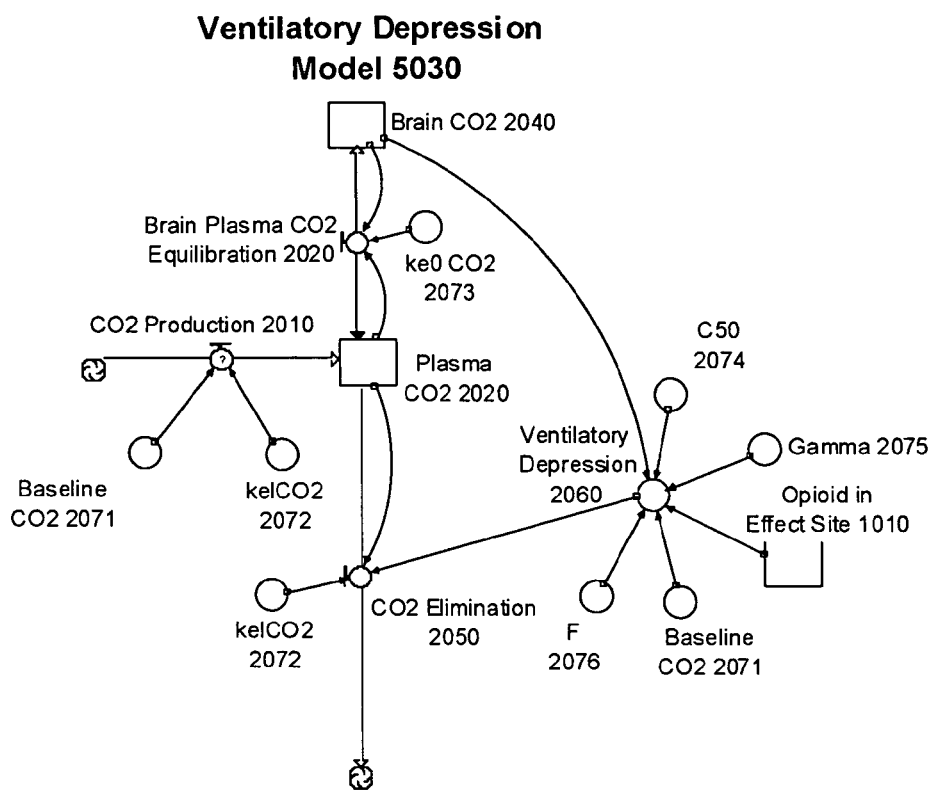
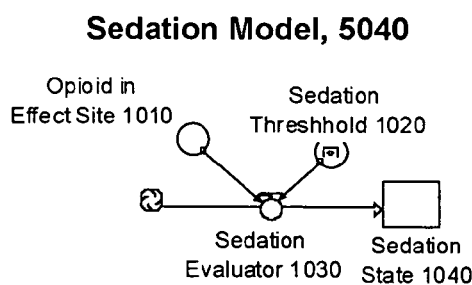

Figure 14: Drug in inhaler and lung in the presence of opioid-induced ventilatory depression and sedation for the two opioid model.
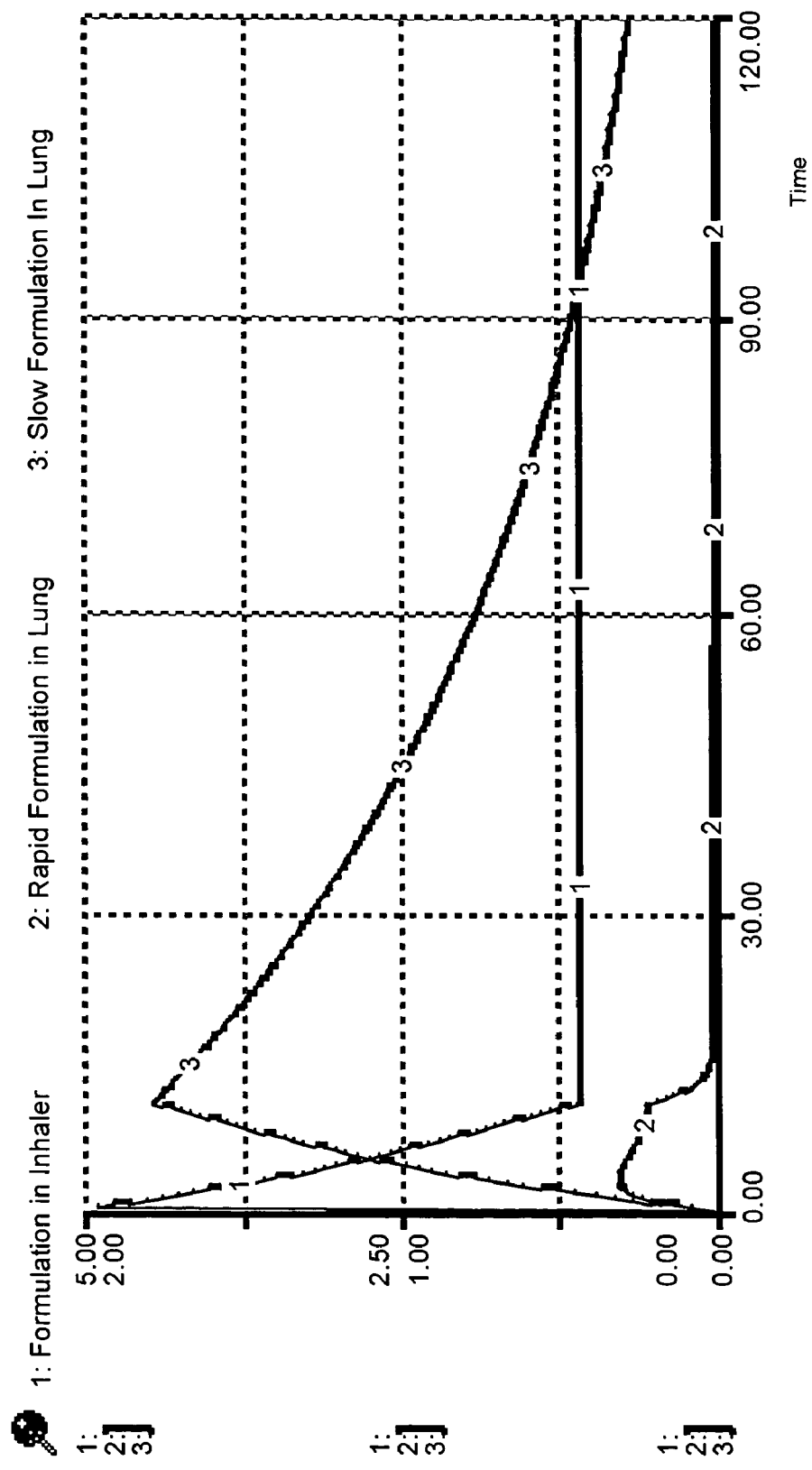

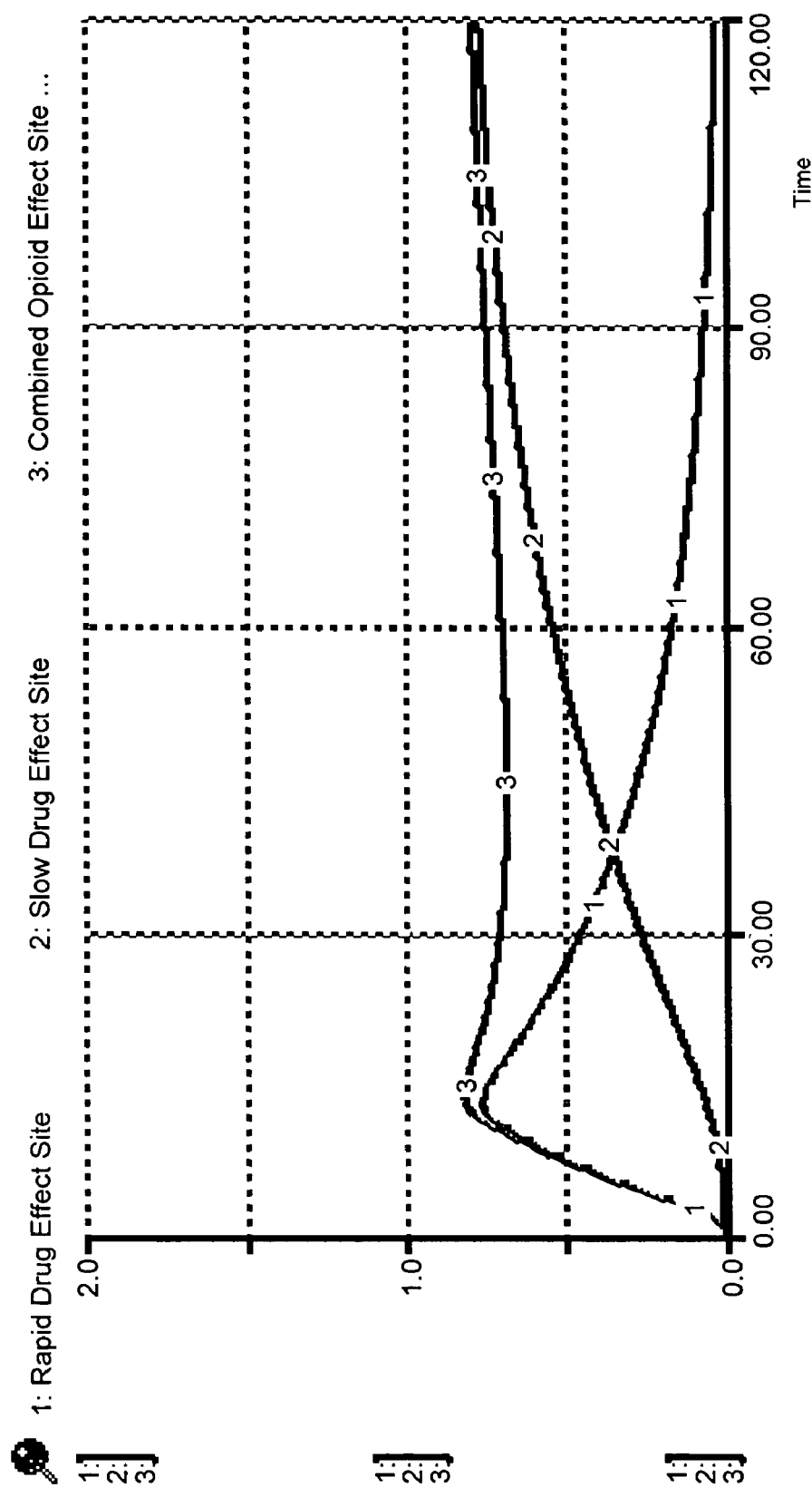
Figure 15: The rapidly acting opioid concentration in the effect site, the slowly acting opioid concentration in the effect site, and the combined concentration of opioid at the effect site, during two opioid administration with the device.

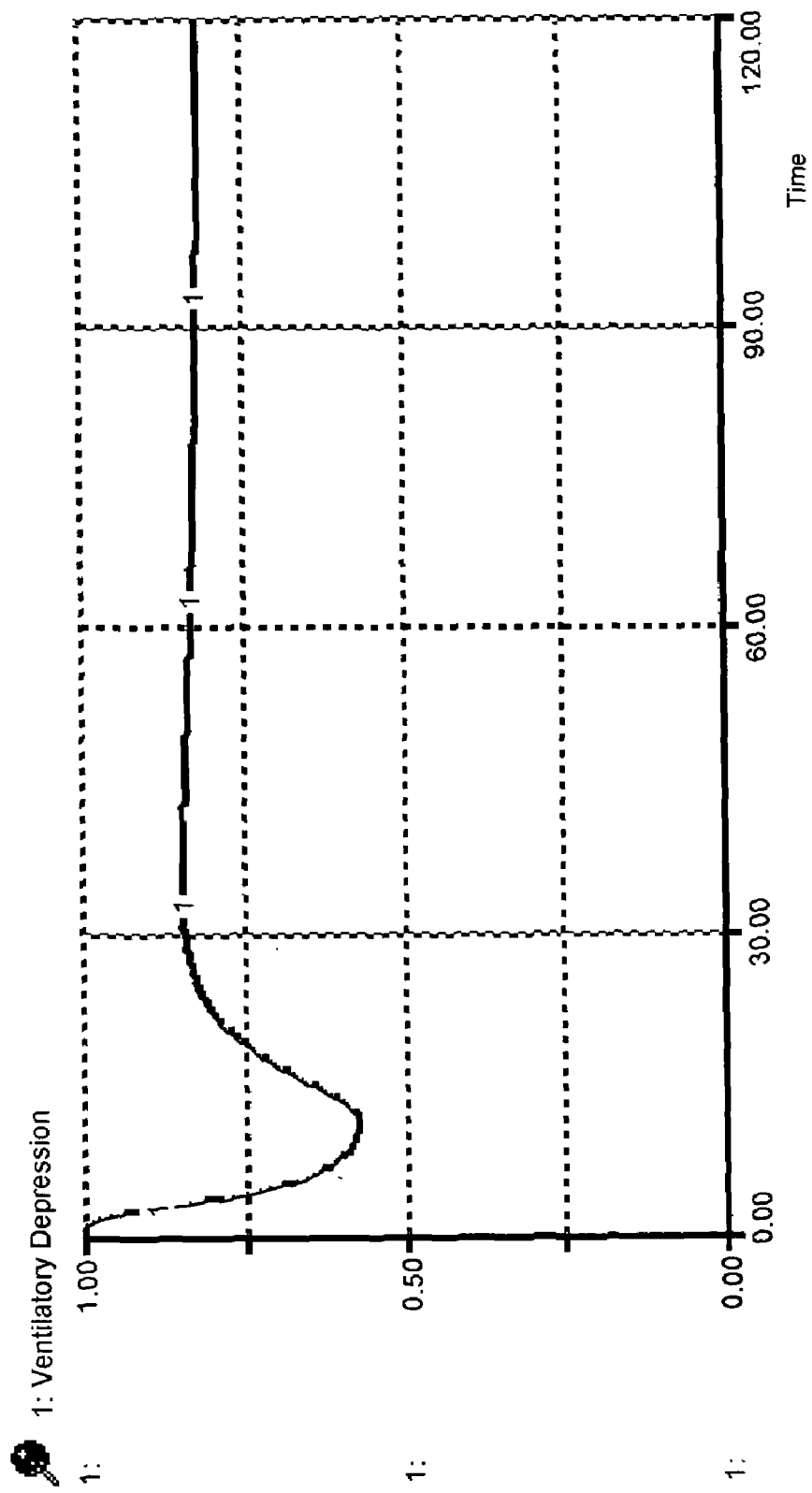
Figure 16: Ventilatory depression in the presence of self-limitation of opioid delivery from ventilatory depression and sedation with the two-opioid delivery system.

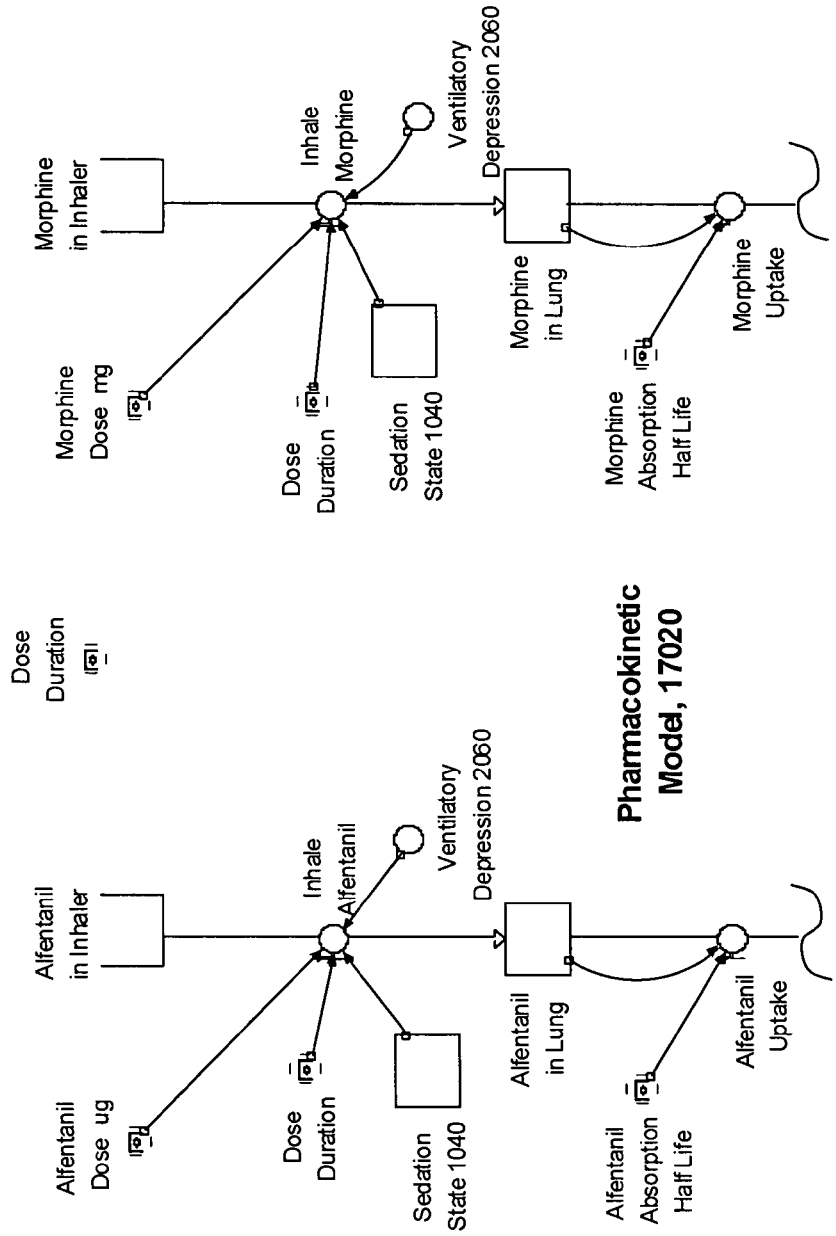
Figure 17A: The elements of the invention, wherein two opioids are administered through inhalation, and the rapidly acting opioid is alfentanil, and the slowly acting opioid is morphine.

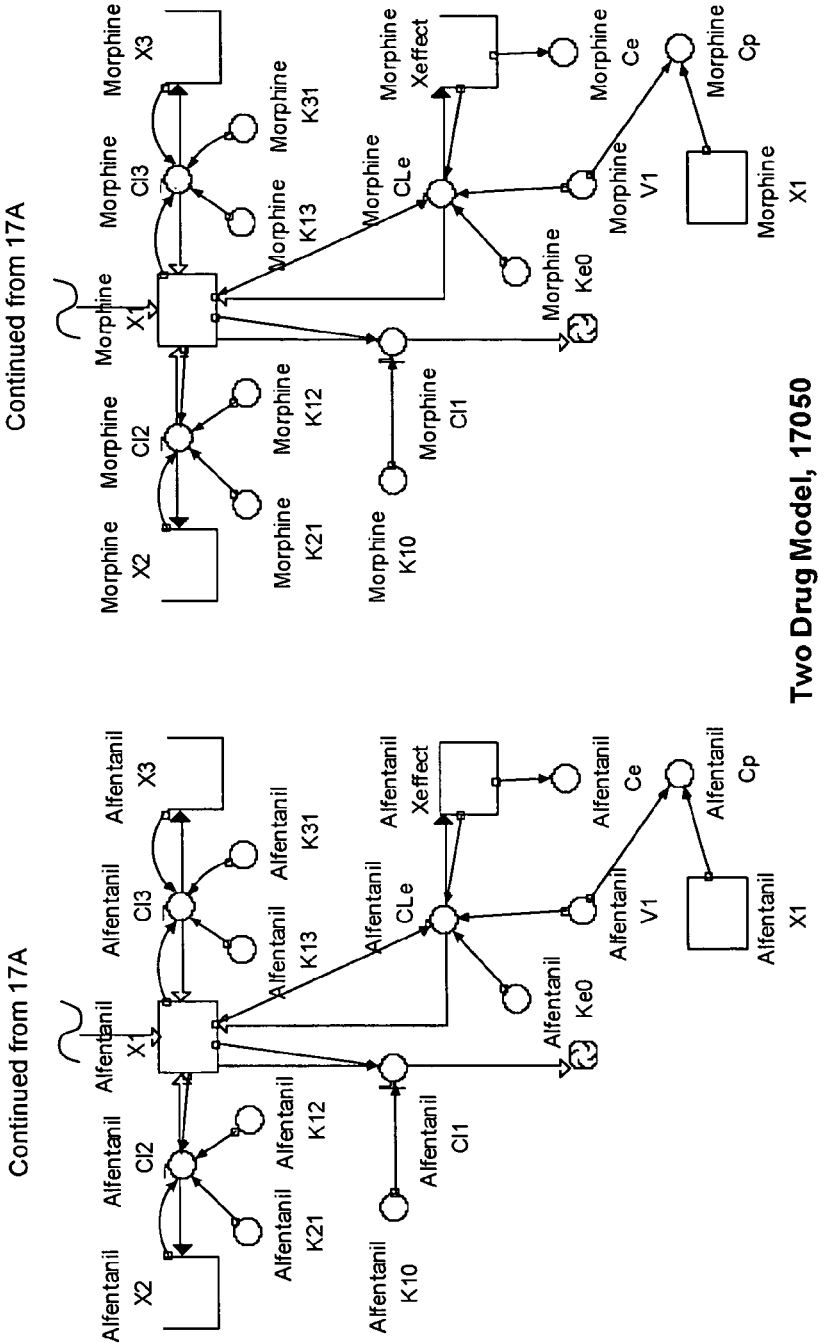
Figure 17B: The elements of the invention, wherein two opioids are administered through inhalation, and the rapidly acting opioid is alfentanil, and the slowly acting opioid is morphine.

Figure 17C: The elements of the invention, wherein two opioids are administered through inhalation, and the rapidly acting opioid is alfentanil, and the slowly acting opioid is morphine.
Two Drug Model, 17050
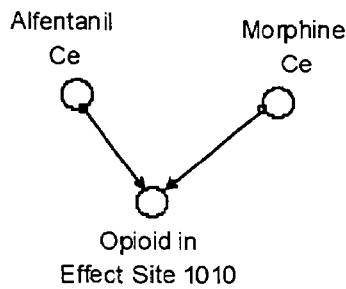
Sedation Model 5040
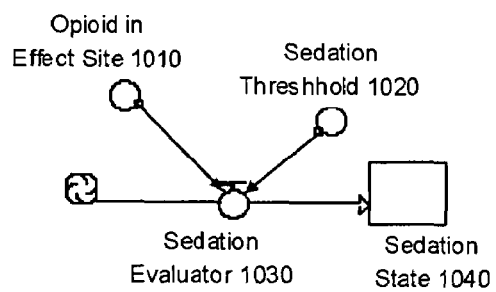
Ventilatory Depression Model 5030
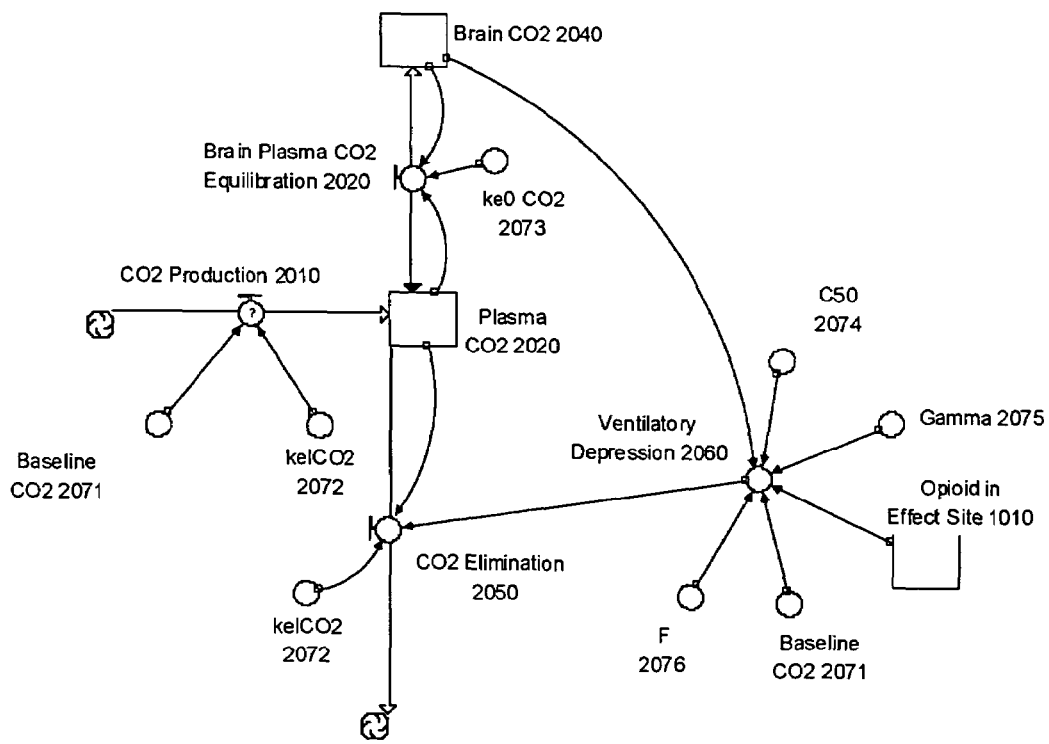

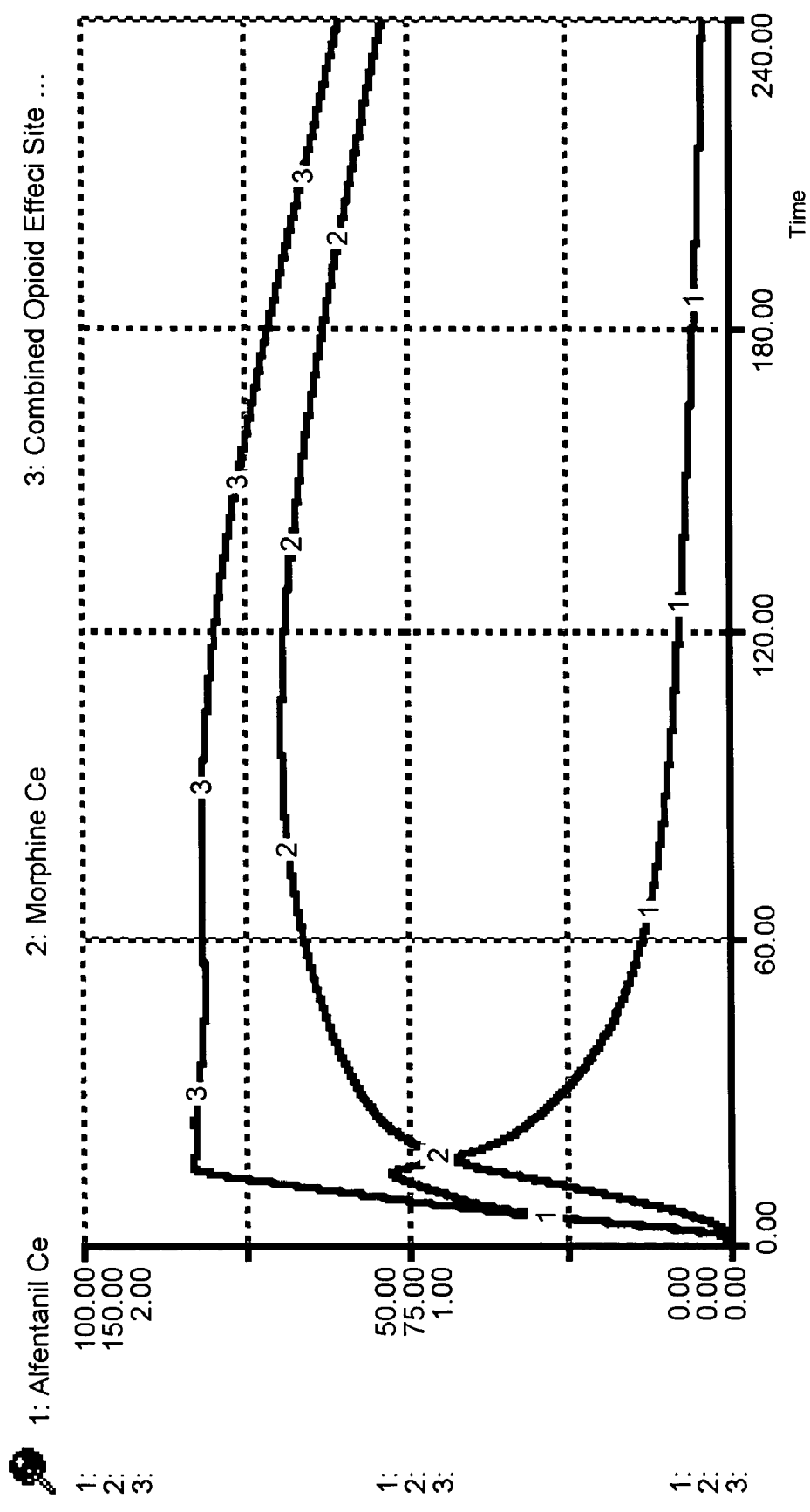
Figure 18: Alfentanil, morphine, and combined opioid effect site concentrations.

Figure 22: Correlation of side effect to toxic event

|            | No side effect | Side effect |    |
|------------|----------------|-------------|----|
| N          | 26             | 24          |    |
| No hypoxia | 22             | 14          | 36 |
| Hypoxia    | 4              | 10          | 14 |
|            |                |             |    |
|            |                |             |    |
| Null effect|                |             |    |
| No hypoxia | 18.72          | 17.28       | 36 |
| Hypoxia    | 7.28           | 6.72        | 14 |
|            |                |             |    |
|            |                |             |    |
| P value    | 0.038653124    |             |    |

OPIOID DELIVERY SYSTEM

This patent is a continuation in part patent application of, and claims priority to, U.S. patent application Ser. No. 10/788,466 filed on Mar. 1, 2004, entitled OPIOID DELIVERY SYSTEM, which, in turn, claims priority to U.S. provisional application 60/450,333, filed on Feb. 28, 2003. The entire text of each of the above patent applications is incorporated by reference into this application.

FIELD OF THE INVENTION

This invention relates to pharmaceutical preparations and methods of administering same and, more particularly, to opioid based analgesics and a method for their administration.

BACKGROUND OF THE INVENTION

Opioids are among the oldest drugs in existence, and remain a mainstay of pain management. Opium, the original opioid, is derived from poppy plants. "Opiates" are natural derivatives of opium, and include morphine, methadone, and heroin. "Opioids" are a broader class of drugs, that includes opium, opiates, and synthetic drugs with the same pharmacological effect of opium. Commonly used synthetic opioids include meperidine, fentanyl, alfentanil, sufentanil, and remifentanil.

Opioids are believed to exert their effects through binding of the mu receptor in the spinal cord and brain, and peripheral tissues. Binding at the mu receptor induces a wide variety of pharmacological effects, including therapeutic effects such as analgesia, effects which may be viewed as either side effects or therapeutic effects, depending on context, including sedation and decreased bowel motility, side effects such as nausea, vomiting, urinary retention, pruritis, ventilatory depression, addiction, and toxicity such as severe ventilatory depression, loss of consciousness and death.

Opioids differ from each other in many ways, including their route of delivery, their physicochemical composition, their drug absorption rate, their pharmacokinetics, and their pharmacodynamics. Noninvasive routes of opioid delivery include oral, rectal, transdermal, transmucosal, and via inhalation. Invasive routes of opioid delivery include intravenous, intramuscular, epidural, spinal, and by injection into joints. When injected intravenously, some opioids quickly enter the brain and spinal cord and thus have a very rapid onset of drug effect (e.g., alfentanil and remifentanil), while others are absorbed slowly to the site of action and have very slow onset of drug effect (e.g., morphine). Similarly, for some opioids the drug effect is very short-lived, owing to very rapid metabolism (e.g., remifentanil), while other opioids may have very slow metabolism and prolonged effect (e.g., methadone). In terms of pharmacodynamics, the potency of opioids covers nearly 5 orders of magnitude, from extraordinarily potent opioids such as carfentanil and etorphine (both used to stun elephants) to relatively less potent drugs such as methadone and morphine. The equivalent potencies of opioids (measured as a "therapeutic equivalence ratio") are well established in the literature, and are often used when changing a patient's treatment regimen from one opioid to another.

Despite these differences, all opioids have the same potential to produce both profound levels of analgesia, and profound toxicity from hypoxia, which can be fatal. Because of the risk of hypoxia, physicians are reluctant to use appropriate doses of opioids to treat acute and chronic pain. As a result, hundreds of thousands of patients who could be provided better pain control receive inadequate doses of opioids. Conversely, even with an understandably cautious approach by the health care community to treatment of pain, every year, many patients die from opioid-induced ventilatory depression.

Pain is highly variable and highly subjective. Different patients respond differently to opioids. As a result, different patients need different amounts of analgesia to treat their pain. As such, it has become desirable to allow patients to vary the amount of analgesic they receive.

One attempt to better adjust opioid dosing in patients has been the introduction of "patient controlled analgesia" ("PCA") (Ballantyne JC, et al. Postoperative patient-controlled analgesia: Meta-analyses of initial randomized control trials. J Clin Anesth 1993:5:182-193.) With the PCA system, the patient must be awake, and must activate a delivery mechanism to receive more opioid, before the drug is given. If the patient becomes overdosed from the opioid, then the patient will become unconscious and not request additional drug. In this manner, the PCA system uses a side effect of opioid, sedation, to limit the amount of opioid given. One problem with the PCA system is that the drug is injected rapidly after the patient requests it (typically, the time frame of administration of drug is under 1 minute) and because the drug most frequently used in the PCA is morphine, a drug that is slowly transferred from the plasma to the site of action—this results in a delay between the patient request for drug and the analgesic effect of the drug. As a result of this delay, patients often request a second (or third) dose of the drug while the opioid effect level of the first injection is still rising. PCA systems include a "lockout" period (commonly 5 minutes), which helps prevent patients from administering more opioid while the opioid drug effect is still rising. Lockout periods are typically controlled, defined or programmed by the health care provider, and there have been many instances where user error or inadvertence in programming the lockout period have resulted in the death of the patient. The patient also often feels frustrated by the lockout, as it diminishes the patients' control of dosing. Other disadvantages of the PCA include the invasive parenteral (intravenous) administration as well as the expensive infusion pumps thus restricting the use of the PCA to institutionalized patients.

A second attempt to better adjust opioid dosing in patients is in the self-administration of Nitrous Oxide during labour associated with childbirth. A nitrous oxide mask is held to the face by the patient during contractions, and is released from the face when adequate analgesia is achieved. However, this mechanism is a titration to analgesic effect and not used as a safety mechanism, since overdosing on nitrous oxide using this system of administration is not a significant concern. Furthermore, nitrous oxide is a gas which requires a heavy steel tank for storage and a complex delivery system for administration. Therefore, the use of nitrous oxide is primarily restricted to the hospital environment and not for ambulatory patients. An additional potential problem with nitrous oxide relates to its low potency and thus the necessity of administering a high concentration (more than 50%) of nitrous oxide in oxygen with a potential of a hypoxic mixture.

The current invention seeks to use two physiological responses of opioids: sedation and ventilatory depression, to limit the total dose of opioids that patients receive. In this manner, the invention seeks to increase safety of opioid drug delivery beyond what is currently accomplished with PCA or other existing opioid administration methods whereby only a single side effect is used to limit the exposure of patients to dangerously high levels of opioid drug effects. The invention also improves the use of sedation by removing the need for a "lockout" period, currently required in PCA systems, and removing the frustration and user error possible therein.

SUMMARY OF THE INVENTION

Accordingly, the invention provides in accordance with a first aspect, an opioid formulation for use in a method of providing analgesia to a patient while avoiding toxicity; said method comprising continuously inhaling the formulation using a pulmonary drug delivery device to produce analgesia, and stopping inhalation when satisfactory analgesia is achieved or at the onset of a side effect; said pulmonary drug delivery device being adapted to deposit particles of the formulation in the lungs at an effective rate; said formulation comprising an effective amount of at least one rapid-onset opioid and at least one sustained-effect opioid, and a pharmaceutically acceptable carrier, the concentration and type of each opioid being selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the patient to terminate inhalation to avoid toxicity.

In one embodiment, the formulation is such that the concentration and type of each opioid is selected so that the maximum total opioid plasma concentration at the onset of side effect is no less than 66%, or no less than 80% of the maximum total opioid plasma concentration.

In another embodiment, the formulation is such that the at least one rapid-onset opioid is fentanyl, alfentanil, sufentanil or remifentanil.

In another embodiment, the at least one sustained-effect opioid is morphine, morphine-6-glucuronide, methadone, hydromorphone, meperidine, an opioid encapsulated in a biocompatible carrier that delays release of the drug at the lung surface, or a liposomally encapsulated opioid. The liposomally encapsulated opioid may be liposomally encapsulated fentanyl.

In one embodiment, the opioid formulation has a total opioid concentration of from 250 to 1500 mcg/ml.

In one embodiment, the opioids in the formulation consist of free fentanyl and liposomally encapsulated fentanyl.

In one embodiment, the ratio of concentration of free fentanyl to liposomally encapsulated fentanyl is 1:5 to 2:1.

In another embodiment, the ratio of concentration of free fentanyl to liposomally encapsulated fentanyl is about 2:3.

In another embodiment, the opioid formulation contains free fentanyl in a concentration of from 100 to 750 mcg/ml.

In another embodiment, the opioid formulation contains liposomally encapsulated fentanyl in a concentration of from 250 to 1500 mcg/ml.

In another embodiment, the opioid formulation has a total opioid concentration of about 500 mcg/ml, a free fentanyl concentration of about 200 mcg/ml and a liposomally encapsulated fentanyl concentration of about 300 mcg/ml.

In another embodiment, the formulation contains two or more different opioids, excluding a formulation wherein the only two opioids are free fentanyl and liposomally encapsulated fentanyl.

In another embodiment, the opioids in the formulation consist of alfentanil and morphine.

In another embodiment, the formulation contains alfentanil in a concentration of from 300 to 6700 mcg/ml.

In another embodiment, the formulation contains morphine in a concentration of from 650 to 13350 mcg/ml.

Another aspect of the invention is a method of administering an opioid formulation to provide analgesia to a patient while avoiding toxicity, comprising the steps of:

continuously inhaling the formulation using a pulmonary drug delivery device adapted to deliver aerosol particles of the formulation into the lungs at an effective rate to produce analgesia; and stopping inhalation when satisfactory analgesia is achieved or at the onset of a side effect;

wherein the formulation comprises an effective amount of at least one rapid-onset opioid and a pharmaceutically acceptable carrier; the concentration and type of each opioid, and effective rate of delivery of the particles being selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the patient to terminate inhalation to avoid toxicity.

In one embodiment, the formulation is dispensed by the pulmonary drug delivery device at a mass median aerodynamic diameter of from 1 to 5 microns.

In another embodiment, the formulation is dispensed by the pulmonary drug delivery device at a mass median aerodynamic diameter of from 1 to 3 microns.

In another embodiment, the formulation is dispensed by the pulmonary drug delivery device at a mass median aerodynamic diameter of from 1.5 to 2 microns.

An other embodiment of the invention is the method wherein the concentration and type of each opioid is selected so that the maximum total opioid plasma concentration at the onset of side effect is no less than 66%, or 80% of the maximum total opioid plasma concentration.

An other embodiment of the invention is the method wherein the at least one rapid-onset opioid is chosen from fentanyl, alfentanil, sufentanil and remifentanil.

An other embodiment of the invention is the method further comprising an effective amount of at least one sustained-effect opioid to provide sustained relief, wherein the concentration and type of each opioid in the formulation is selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the patient to terminate inhalation to avoid toxicity.

An other embodiment is the method wherein the at least one sustained-effect opioid is chosen from morphine, morphine-6-glucuronide, methadone, hydromorphone, meperidine, an opioid encapsulated in a biocompatible carrier that delays release of the drug at the lung surface, and a liposomally encapsulated opioid.

Another embodiment is the method wherein the liposomally encapsulated opioid is liposomally encapsulated fentanyl.

Another embodiment is the method wherein the at least one sustained-effect opioid is chosen from morphine and liposomally encapsulated fentanyl.

Another embodiment is the method wherein the opioids in the formulation consist of free fentanyl and liposomally encapsulated fentanyl.

Another embodiment is the method wherein the ratio of concentration of free fentanyl to liposomally encapsulated fentanyl is from 1:5 to 2:1.

Another embodiment is the method wherein the ratio of concentration of free fentanyl to liposomally encapsulated fentanyl is about 2:3.

Another embodiment is the method wherein the total opioid concentration is from 250 to 1500 mcg/ml.

Another embodiment is the method wherein the formulation comprises free fentanyl in a concentration of from 100 to 750 mcg/ml.

Another embodiment is the method wherein the formulation comprises liposomally encapsulated fentanyl in a concentration of from 250 to 1500 mcg/ml.

Another embodiment is the method wherein the total opioid concentration is about 500 mcg/ml, the free fentanyl concentration is about 200 mcg/ml and the liposomally encapsulated fentanyl concentration is about 300 mcg/ml.

Another embodiment is the method wherein from 4 to 50 mcg/min. of free fentanyl is deposited in the lungs during inhalation.

Another embodiment is the method wherein from 10 to 20 mcg/min. of free fentanyl is deposited in the lungs during inhalation.

Another embodiment is the method wherein about 15 mcg/min. of free fentanyl is deposited in the lungs during inhalation.

Another embodiment is the method wherein from 5 to 150 mcg/min. of liposomally encapsulated fentanyl is deposited in the lungs during inhalation.

Another embodiment is the method wherein from 10 to 90 mcg/min. of liposomally encapsulated fentanyl is deposited in the lungs during inhalation.

Another embodiment is the method wherein from 15 to 60 mcg/min. of liposomally encapsulated fentanyl is deposited in the lungs during inhalation.

Another embodiment is the method wherein from 20 to 45 mcg/min. of liposomally encapsulated fentanyl is deposited in the lungs during inhalation.

Another embodiment is the method wherein from 5 to 100 mcg/min. of total opioid is deposited in the lungs during inhalation.

Another embodiment is the method wherein from 10 to 40 mcg/min. of total opioid is deposited in the lungs during inhalation.

Another embodiment is the method wherein from 30 to 35 mcg/min. of total opioid is deposited in the lungs during inhalation.

Another embodiment is the method wherein the formulation comprises two or more different opioids, excluding a formulation wherein the only two opioids are free fentanyl and liposomally encapsulated fentanyl.

Another embodiment is the method wherein the administration takes place over between 50 and 500 inhalations.

Another embodiment is the method wherein the opioids in the formulation consist of alfentanil and morphine.

Another embodiment is the method wherein the formulation contains alfentanil in a concentration of from 300 to 6700 mcg/ml.

Another embodiment is the method wherein from 100 to 500 mcg/min of alfentanil is deposited in the lungs during inhalation.

Another embodiment is the method wherein about 250 mcg/min of alfentanil is deposited in the lungs during inhalation.

Another embodiment is the method wherein the formulation contains morphine in a concentration of from 650 to 13350 mcg/ml.

Another embodiment is the method wherein from 100 to 2000 mcg/min of morphine is deposited in the lungs during inhalation.

Another embodiment is the method wherein from 200 to 1000 mcg/min of morphine is deposited in the lungs during inhalation.

Another embodiment is the method wherein about 500 mcg/min of morphine is deposited in the lungs during inhalation.

Another aspect of the invention is the use of a side effect of an opioid in preventing opioid toxicity.

Another aspect of the invention is a pulmonary drug delivery device containing an opioid formulation for producing analgesia in a patient, comprising:

a container containing a formulation as described above;

an outlet coupled to the container;

means coupled to the container for dispensing particles of said formulation through said outlet and into the lungs through actuation by conscious patient effort and at an effective rate whereby, during inhalation, analgesia is achieved before the onset of an opioid side effect, and the onset of said side effect occurs before the onset of toxicity, and so that the maximum total opioid plasma concentration does not reach toxic levels, and whereby the onset of said side effect can be used by the patient to terminate inhalation to avoid toxicity.

Another aspect of the invention is a pulmonary drug delivery device containing an opioid formulation for producing analgesia in a patient, said device comprising:

a container containing a formulation comprising an effective amount of at least one rapid-onset opioid and a pharmaceutically acceptable carrier;

an outlet coupled to the container;

means coupled to the container for dispensing particles of said formulation through said outlet and into the lungs, said means requiring conscious patient effort to be actuated;

wherein the concentration and type of each opioid and effective rate of delivery of the particles are selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the patient to terminate inhalation to avoid toxicity.

Another embodiment is the device further comprising delivery rate controlling means for limiting the rate at which the formulation is dispensed to below a selected threshold.

Another embodiment is the device wherein the outlet comprises a fenestration which must be sealed by the lips of the patient in order for the formulation to be dispensed.

Another embodiment is the device wherein the dispensing means is breath actuated.

Another embodiment is the device wherein the particles have a mass median aerodynamic diameter of from 1 to 5 microns.

Another embodiment is the device wherein the particles have a mass median aerodynamic diameter of from 1 to 3 microns.

Another embodiment is the device wherein said particles have a mass median aerodynamic diameter of from 1.5 to 2 microns.

Another embodiment is the device wherein the concentration and type of each opioid is selected so that the maximum total opioid plasma concentration at the onset of side effect is no less than 66% of the maximum total opioid plasma concentration.

Another embodiment is the device wherein the concentration and type of each opioid is selected so that the maximum total opioid plasma concentration at the onset of side effect is no less than 80% of the maximum total opioid plasma concentration.

Another embodiment is the device wherein the at least one rapid-onset opioid is chosen from fentanyl, alfentanil, sufentanil and remifentanil.

Another embodiment is the device further comprising an effective amount of at least one sustained-effect opioid to provide sustained relief, wherein the concentration and type of each opioid in the formulation is selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the patient to terminate inhalation to avoid toxicity.

Another embodiment is the device wherein the at least one sustained-effect opioid is chosen from morphine, morphine-6-glucuronide, methadone, hydromorphone, meperidine, an opioid encapsulated in a biocompatible carrier that delays release of the drug at the lung surface, and a liposomally encapsulated opioid.

Another embodiment is the device wherein the liposomally encapsulated opioid is liposomally encapsulated fentanyl.

Another embodiment is the device wherein the at least one sustained-effect opioid is chosen from morphine and liposomally encapsulated fentanyl.

Another embodiment is the device wherein the opioids in the formulation consist of free fentanyl and liposomally encapsulated fentanyl.

Another embodiment is the device wherein the ratio of concentration of free fentanyl to liposomally encapsulated fentanyl is from 1:5 to 2:1.

Another embodiment is the device wherein the ratio of concentration of free fentanyl to liposomally encapsulated fentanyl is about 2:3.

Another embodiment is the device wherein the total opioid concentration is from 250 to 1500 mcg/ml.

Another embodiment is the device wherein the formulation comprises free fentanyl in a concentration of from 100 to 750 mcg/ml.

Another embodiment is the device wherein the formulation comprises liposomally encapsulated fentanyl in a concentration of from 250 to 1500 mcg/ml.

Another embodiment is the device wherein the total opioid concentration is about 500 mcg/ml, the free fentanyl concentration is about 200 mcg/ml and the liposomally encapsulated fentanyl concentration is about 300 mcg/ml.

Another embodiment is the device wherein from 4 to 50 mcg/min. of free fentanyl is deposited in the lungs during inhalation.

Another embodiment is the device wherein from 10 to 20 mcg/min. of free fentanyl is deposited in the lungs during inhalation.

Another embodiment is the device wherein about 15 mcg/min. of free fentanyl is deposited in the lungs during inhalation.

Another embodiment is the device wherein from 5 to 150 mcg/min. of liposomally encapsulated fentanyl is deposited in the lungs during inhalation.

Another embodiment is the device wherein from 10 to 90 mcg/min. of liposomally encapsulated fentanyl is deposited in the lungs during inhalation.

Another embodiment is the device wherein from 15 to 60 mcg/min. of liposomally encapsulated fentanyl is deposited in the lungs during inhalation.

Another embodiment is the device wherein from 20 to 45 mcg/min. of liposomally encapsulated fentanyl is deposited in the lungs during inhalation.

Another embodiment is the device wherein from 5 to 100 mcg/min. of total opioid is deposited in the lungs during inhalation.

Another embodiment is the device wherein from 10 to 40 mcg/min. of total opioid is deposited in the lungs during inhalation.

Another embodiment is the device wherein from 30 to 35 mcg/min. of total opioid is deposited in the lungs during inhalation.

Another embodiment is the device wherein the formulation comprises two or more different opioids, excluding a formulation wherein the only two opioids are free fentanyl and liposomally encapsulated fentanyl.

Another embodiment is the device wherein the opioids in the formulation consist of alfentanil and morphine.

Another embodiment is the device wherein the formulation contains alfentanil in a concentration of from 300 to 6700 mcg/ml.

Another embodiment is the device wherein from 100 to 500 mcg/min of alfentanil is deposited in the lungs during inhalation.

Another embodiment is the device wherein about 250 mcg/min of alfentanil is deposited in the lungs during inhalation.

Another embodiment is the device wherein the formulation contains morphine in a concentration of from 650 to 13350 mcg/ml.

Another embodiment is the device wherein from 100 to 2000 mcg/min of morphine is deposited in the lungs during inhalation.

Another embodiment is the device wherein the means dispenses between 0.2% to 1% of the formulation per inhalation.

Another embodiment is the device wherein from 200 to 1000 mcg/min of morphine is deposited in the lungs during inhalation.

Another embodiment is the device wherein about 500 mcg/min of morphine is deposited in the lungs during inhalation.

Another aspect of the invention is an opioid administration kit comprising:

a pulmonary drug delivery device as described above; and instructions for using said device comprising the steps of continuously inhaling the formulation using said device and stopping inhalation when satisfactory analgesia is achieved or at the onset of a side effect.

Another aspect of the invention is an opioid administration kit comprising:

a formulation comprising an effective amount of at least one rapid-onset opioid and a pharmaceutically acceptable carrier;

a pulmonary drug delivery device comprising a container, an outlet coupled to the container, means coupled to the container for dispensing particles of formulation contained therein through said outlet and into the lungs through actuation by conscious patient effort and at an effective rate whereby, during inhalation, analgesia is achieved before the onset of an opioid side effect, and the onset of said side effect occurs before the onset of toxicity, and so that the maximum total opioid plasma concentration does not reach toxic levels, and whereby the onset of said side effect can be used by the patient to terminate inhalation to avoid toxicity; and instructions for using said device comprising the steps of filling the container with the formulation, continuously inhaling the formulation using said device, and stopping inhalation when satisfactory analgesia is achieved or at the onset of a side effect.

Another embodiment is the opioid administration kit wherein said formulation comprises and effective amount of at least one sustained-effect opioid.

Another aspect of the invention is an opioid formulation for use in a method of providing analgesia to a patient, comprising:

150 to 250 mcg/ml of free fentanyl;
200 to 400 mcg/ml of liposomally encapsulated fentanyl; and
a pharmaceutically acceptable carrier.

Another aspect of the invention is an opioid formulation for use in a method of providing analgesia to a patient through a pulmonary route of administration, comprising:

two or more different opioids, excluding a formulation wherein the only two opioids are free fentanyl and liposomally encapsulated fentanyl;
a pharmaceutically acceptable carrier.

In accordance with further aspects of the invention, there is provided a use of the present formulation in providing analgesia to a patient and in the manufacture of a medicament for doing same.

Useful drug formulations and parameters for administration according to the present invention can be determined by the person skilled in the art based on known pharmacological data as well as through pharmacokinetic and pharmacodynamic modeling as herein described. Such modeling is intended to ensure that analgesic effect is achieved before the onset of a side effect, and that the onset of the side effect occurs well in advance of toxicity, and to ensure that once the patient stops inhaling the formulation, there will not be a continued rise in total opioid concentration in the plasma to toxic levels.

BRIEF DESCRIPTION OF THE DRAWINGS

FIG. 1 is a flow diagram which represents a computer simulation model for sedation.

FIG. 2 is a flow diagram which represents a computer simulation model for ventilatory depression.

FIG. 3 is a flow diagram which represents a computer simulation model for an inhalation device.

FIG. 4 is a flow diagram which represents a computer simulation model for the pharmacokinetic profiling of opioid as administered to a patient through a pulmonary route.

FIGS. 5A and 5B, taken together, are a flow diagram which represents the Stella™ computer simulation of the pharmacokinetics of the administration of a single opioid. FIG. 5A shows the Device Model and Pharmacokinetic Model aspects of the simulation, FIG. 5B shows the Ventilatory Depression Model and the Sedation Model aspects of the simulation.

FIG. 12 is a flow diagram which represents a computer simulation model for the administration of two opioids.

FIGS. 13A, 13B and 13C, taken together, are a flow diagram which represents the Stella™ computer simulation of the pharmacokinetics of the administration of two opioids.

FIG. 14 is a graph showing the output of Stella™ computer simulation of FIGS. 13A, 13B and 13C expressed as a time course of total quantity of opioid in the inhalation device and in the lung of the patient (ventilatory depression and sedation models enabled).

FIG. 15 is a graph showing the time course of concentration of each opioid and of total opioid at the effect site in the Stella™ computer simulation of FIGS. 13A, 13B and 13C (ventilatory depression and sedation models enabled).

FIG. 16 is a graph showing the time course of ventilatory depression during and after delivery of opioids in the Stella™ computer simulation of FIGS. 13A, 13B and 13C (ventilatory depression and sedation models enabled).

FIGS. 17A, 17B and 17C, taken together, are a flow diagram which represents the Stella™ computer simulation of the pharmacokinetics of the administration of two opioids, where the two opioids being administered are alfentanil and morphine. FIGS. 17A and 17B show the Device Model and Pharmacokinetic Model aspects of the simulation, while FIG. 17C shows the Ventilatory Depression Model, Sedation Model, and Two Drug Model aspects of the simulation.

FIG. 18 is a graph showing the time course of concentration of alfentanil, morphine, and combined opioid at the effect site in the Stella™ computer simulation of FIGS. 17A, 17B and 17C (ventilatory depression and sedation models enabled).

FIG. 20 is a graph showing maximum concentration of opioid in the plasma against end of dose concentration of opioid in the plasma of patients administered opioid.

FIG. 22 is a table showing the statistical correlation of side effect to toxic effect.

DETAILED DESCRIPTION OF THE INVENTION

Figure 6:
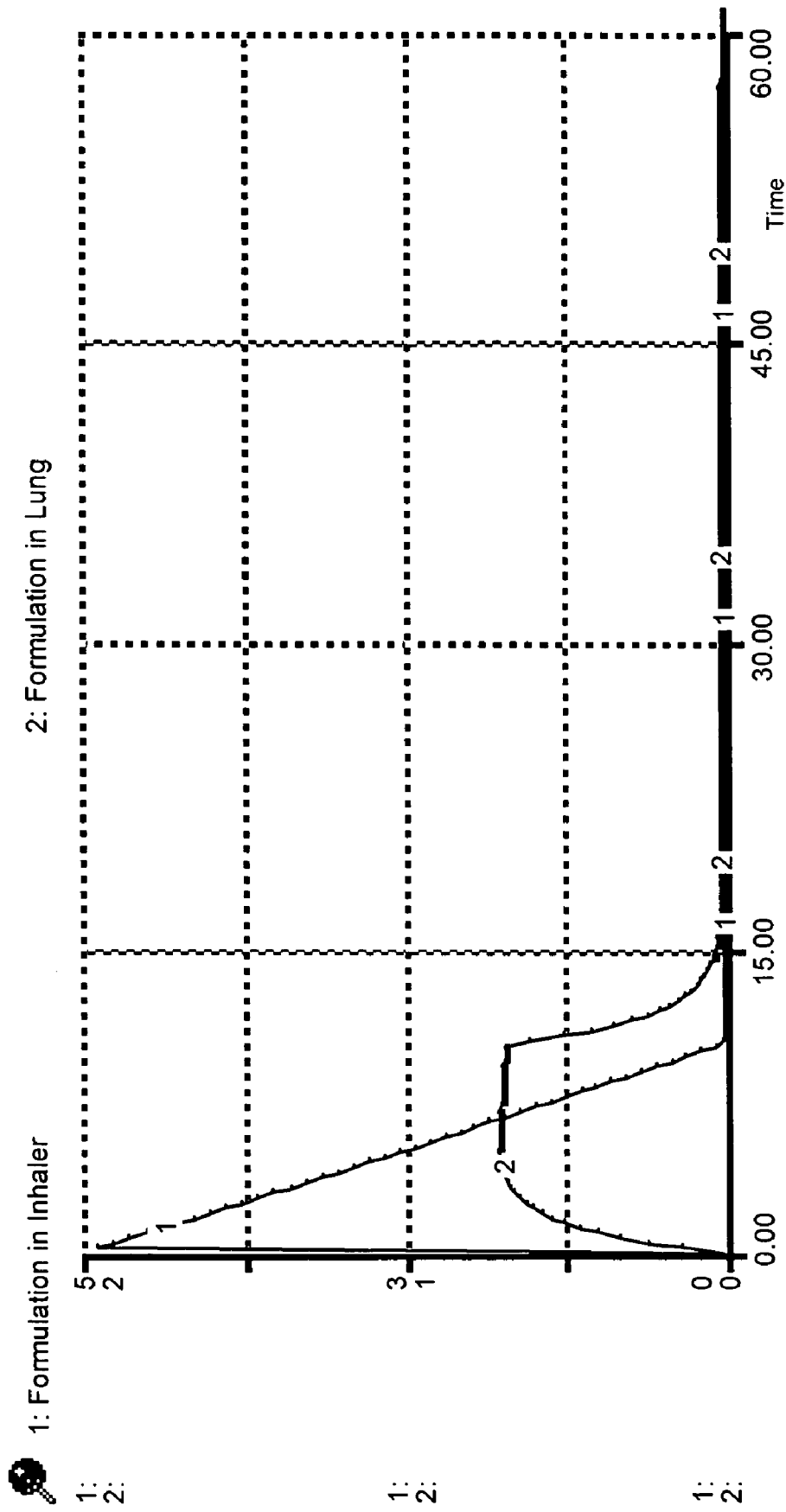
FIG. 6 is a graph showing output of the Stella™ computer simulation of FIGS. 5A and 5B (ventilatory depression and sedation models disabled) expressed as a time course of quantity of opioid in the inhalation device and in the lung of the patient.

In this application, the following terms have the following meanings:

"Analgesic effect" or "analgesia" means the relief from pain resulting from the action of a drug.

"Drug delivery profile" means the concentration of the drug, over time, at the site of drug effect, as determined by the amount and rate of drug administered to the patient and the pharmacokinetics relating dose inhaled to concentration in the lungs, plasma and at the site of drug effect.

"Hypoxia" is a toxic effect of opioid administration, and is defined in this application as a decrease in blood O2 concentration to less than 90% saturation.

"Ventilatory depression" means a decrease in the rate, tidal volume, and/or flow rate of air into the lungs. Ventilatory depression may manifest as dizziness, shortness of breath, or a slowing in rate of breathing. "Opioid induced ventilatory depression" refers to ventilatory depression caused by the action of an opioid at a site of drug effect.

"Sedation" means a decrease in attention, mental awareness, focus, and state of consciousness caused by opioids, and manifests in a lack of physical strength (muscle fatigue), lack of voluntary activity, lethargy, drowsiness, and sleep. "Opioid-induced sedation" refers to sedation caused by the action of an opioid at a site of drug effect.

"Rapid onset", when used to describe a drug formulation, means a formulation which has an analgesic effect that rapidly follows the rise in plasma opioid concentration. A "rapid onset opioid" is an opioid that has an analgesic effect within 5 minutes of administration.

"Sustained effect" means a formulation which has an analgesic effect that is sustained over several hours. A "sustained effect opioid" means an opioid that has analgesic effect that lasts over 2 hours.

"Side effect" means an effect of an opioid that is not analgesic or toxic. For example, severe ventilatory depression is an example of opioid toxicity, while mild ventilatory depression and sedation are not considered signs of opioid toxicity, but are side effects of the opioid.

"Site of effect" refers to a physical or hypothetical site of drug action within the patient. "Site of effect" may be a compartment of the body, such as the brain, the liver, or the spleen, or it may be a theoretical and unknown location based on correlation and pharmacokinetic modeling. For example, it is known that opioids exert their analgesic actions, in part, in the substantia gelatinosa of the spinal cord, so this is a site of opioid analgesic effect. The concentration of opioid at the effect site may be determined by direct measurement, or through the use of pharmacokinetic and pharmacodynamic modeling.

"Effective amount" means the amount of drug needed to reach an analgesic effect.

"mass median aerodynamic diameter" means the aerodynamic diameter an aerosol such that half of the cumulative mass of all particles is contained in particles with smaller (or larger) diameters and wherein the aerodynamic diameter is defined as the diameter of a unit-density sphere having the same gravitational settling velocity as the particle being measured.

"breathing rate" means the number of breaths taken per unit of time.

"Titration to effect" means administering an opioid until a satisfactory analgesic effect is felt by the patient, then ceasing administration of the opioid.

"Titration to side effect" means administering an opioid until a side effect is felt, then ceasing administration. The ceasing of administration may be voluntary (for example, by instructing patients to cease administration of the opioid when they start to feel drowsy, dizzy or short of breath) or involuntary (for example, when patients are no longer able to breathe effective dosages of opioid due to ventilatory depression or sedation).

The terms "toxic", "toxicity", "toxic effect" and "opioid toxicity" refer to effects of opioids that place a patient at risk of death. For example, opioids commonly produce modest amounts of ventilatory depression that pose little risk to a patient. This is not considered an example of opioid toxicity. However, severe ventilatory depression poses the risk of hypoxia, loss of consciousness, and death. Thus, severe ventilatory depression is an example of opioid toxicity, while mild ventilatory depression is not considered a sign of opioid toxicity.

The present invention is for use in patient self-administration of opioids. The invention utilizes the opioid's side effects to self-regulate the amount of opioid given to a patient, thereby tailoring the dose to achieve the patient's analgesic requirements, while avoiding toxicity and death.

The use of the invention begins with the patient's perception of pain. There are many modalities of treating mild to moderate pain, but opioids are the mainstay of treatment for moderate to severe pain. In response to the moderate or severe pain, either the patient or the patient's care provider open a prefilled vial of opioid in liquid solution, or, alternatively, in an emulsion. The liquid is added to a nebulizer.

The nebulizer is then brought to the mouth, and is held there with the hand. The nebulizer is not attached to the face with straps, as this prevents the self-limiting mechanism from working.

With each breath, the nebulizer releases a small amount of the liquid opioid as an aerosol. The aerosol passes through the patient's mouth and into the trachea and lungs, where the aerosolized opioid is deposited.

Throughout this patent application, the nebulizer is also called an inhaler or an aerosol pulmonary drug delivery device. An inhaler may refer to either a nebulizer or a nebulizer combined with a source of compressed air or oxygen, or any other aerosol generating device for the administration of drug by way of the lungs. An aerosol pulmonary drug delivery device refers to any device that allows the aerosolization of a substance for delivery into the lungs. Various nebulizer technologies are known and available in the art.

The rate of onset of opioid drug effect is believed to be dictated by the speed at which the opioid enters the lungs, the rate of absorption into the systemic circulation and the rate at which the opioid crosses the blood brain barrier. Some opioids, such as alfentanil and remifentanil, cross the blood brain barrier very quickly, and thus produce very rapid onset of drug effect. Other opioids, such as morphine and morphine-6-glucuronide, cross the blood brain barrier very slowly, and thus produce a slow onset but sustained effect.

As the opioid crosses the blood brain barrier, it starts to exert effects at the site of drug action. Although in some instances, patients may feel effects differently, typically, as concentration of opioid increases, the effects felt are analgesic effect, side effect, and toxic effect, in that order.

Ventilatory depression is up and down regulated by the opposing actions of opioids (which depress ventilation) and carbon dioxide (which increases ventilation). This occurs in a feedback loop as follows: initially the opioids will depress ventilation. Because the patient is not exhaling as much carbon dioxide, the level of carbon dioxide in the patient's blood will rise. As the carbon dioxide rises, it stimulates ventilation, partly offsetting the opioid-induced ventilatory depression. The opioid-induced ventilatory depression must come on sufficiently rapidly so that it occurs as the patient is inhaling the opioid, thus serving to limit the amount of opioid inhaled. However, it must not come on so rapidly as to place the patient at risk of toxic effects before the carbon dioxide has had a chance to rise and offset the opioid induced ventilatory depression.

The amount of opioid inhaled by the patient each minute is proportional to the ventilation during that minute. As ventilation becomes depressed, the rate of opioid delivery to the lungs is depressed proportionally. In this way, the rate of delivery is slowed by ventilatory depression, decreasing the ability of the patient to self-administer a toxic dose of opioid.

The slowed uptake of opioid from ventilatory depression creates the opportunity for complete cessation of drug delivery through the onset of sedation.

As the opioids exert their analgesic effects, patients will become sedated, in part from the mitigation of their pain, in part due to the side effects of the opioids. As sedation develops in patients, it becomes difficult to hold the device to the mouth, maintain a seal with the lips, and breathe through the device to administer additional opioid. Instead, the patient begins to breathe through the nose, or through the mouth but around the mouthpiece of the nebulizer. With increasing sedation, the arm drops away from the airway, removing the device from the mouth. This dropping away of the arm may be encouraged to take place at a lower level of sedation by making the device deliberately heavy, or by adding a weight to the device. Weight of the device can be adjusted from patient to patient, depending on the individual patient's strength pre-sedation.

Since the side effects of the opioids typically occur at lower opioid concentrations (as compared to the opioid toxic effects), a safer, patient self-limited opioid administration has been created through the pulmonary administration of an opioid (or a combination of opioids) at a rate sufficiently slow to allow for a time gap between the onset of side effects and the onset of toxic effects. The rate must also be slow enough (as compared to the rate of onset of the opioid) to allow for the onset of side effects while the dose is being administered.

In a clinical study relating to this invention, healthy subjects were directed to inhale a fixed dose of the fentanyl formulation consisting of rapidly acting free fentanyl and sustained acting liposomal encapsulated fentanyl over 10-25 minutes. In this study, several subjects attempted to self-limit the dose and required external assistance to receive the entire dose. Some subjects self-limited the dose because of opioid-induced ventilatory depression, with a decrease in ventilation rate reducing the amount of drug inhaled. Other subjects self-limited the dose because of sedation, and their inability to hold the device to the mouth to continue inhaling fentanyl. Some subjects exhibited both side effects. The trial demonstrated that patient will, in fact, self-limit fentanyl administration via the pulmonary route before a toxic level of fentanyl is administered, when 1) the drug is intended to be inhaled over a deliberately extended period of time (e.g. up to 25 minutes), 2) opioid induced ventilatory depression occurs while the drug is being given (and before a toxic dose is administered), and/or 3) sedation occurs while the drug is being given (and before a toxic dose is administered). We have found that these factors can be controlled by designing the rate at which an opioid is given to a patient accordingly.

Preferably, the opioid formulation is administered over 4-25 minutes. The total amount of opioid administered over the 4-25 minutes will depend on several factors, including the type of opioid or combination of opioids delivered, and the mass median aerodynamic diameter (MMAD) of the particles being inhaled. This administration period results in a rate of onset to effect that is influenced by the rate of administration and affords the patient the ability to involuntarily self-limit the dose through the onset of ventilatory depression and sedation. We have found that, for an alfentanil/morphine combination drug, a range of 100-500 mcg/min of alfentanil and 200-1000 mcg/min of morphine is optimal (measured as drug delivered to the lung of the patient ("systemically available drug")).

For a free and liposomally encapsulated fentanyl formulation, we have found that the levels for systemically available drug to be optimum at 10-25 mcg/min of free fentanyl and 10-50 mcg/min of liposomally encapsulated fentanyl.

For other opioid formulations, we expect that a therapeutically equivalent rate of systemically available drug to have similar advantages.

In order to prevent peaks of opioid effect that are more potent than the concentration at which patients stop taking the drug in a multiple opioid formulation with at least one rapid-onset opioid and at least one sustained effect opioid, we expect that the ratio of sustained-effect opioid to rapid-onset opioid administered should be less than 1:1 in terms of therapeutic equivalent potency.

Another factor affecting the rate of administration of opioid is the patient's breathing rate. We have found that a breathing rate of 10-15 breaths per minute (i.e. a "normal" breathing rate) is preferred.

Opioid response is highly individualized. This reflects, in part, varying levels of painful stimulation. In the presence of very severe pain, very high doses of opioids can be administered without undue toxicity. Patients being administered chronic opioids require higher doses to produce both the desired therapeutic effects and opioid toxicity. This also reflects the development of tolerance to opioids. Physicians have sought improved means of administering opioids in part because of the wide range of doses required to adequately tailor the opioid to the needs of individualized patients.

With the described invention, patients who need large doses of opioids to provide analgesia can elect to administer either a larger volume of drug (inhaled over a longer period of time), or can be offered a more concentrated solution of drug to be inhaled over the expected 4-25 minutes. Either way, the opioid-induced ventilatory depression and sedation will still attenuate, and eventually terminate, drug administration before toxic doses are inhaled. Preferably, the patient will inhale the drug over a longer period of time. Conversely, a patient who requires only a small dose will experience the desired pain relief after a shorter inhalation period. The patient can elect to not inhale additional drug. The patient who unwisely continues to self-administer opioid despite obtaining the desired pain relief will experience ventilatory depression and sedation, which will then either voluntarily (according to the instructions given to the patient) or involuntarily (due to the side effects themselves) attenuate and subsequently terminate drug administration before inhalation of a toxic dose of opioid. The patient is therefore empowered to self-titrate to analgesic effect, without a lockout period and with a lower risk of toxicity.

The selection of opioid and opioid concentration (as disclosed above, or otherwise) for the device requires consideration of the time course of opioid absorption from the lung into the plasma, and the time course of opioid transfer from the plasma into the site of drug effect (e.g., the brain or spinal cord).

Some opioids are associated with very rapid absorption from the lung into the systemic circulation. For example, the absorption of free fentanyl from the lung into the plasma is nearly instantaneous. This would likely be true of remifentanil, alfentanil, and sufentanil as well. The absorption of free fentanyl released from the liposomal encapsulated fentanyl from the lung to the plasma is far slower.

Some opioids are associated with very rapid transfer from the plasma to the site of drug effect. For example, peak alfentanil and remifentanil concentrations at the site of drug effect occur within 2 minutes of intravenous injection. Other opioids are associated with very slow transfer from the plasma to the site of drug effect. For example, the peak drug effect from an intravenous dose of morphine may be delayed by 10-15 minutes from the time of the injection.

For the self limiting opioid delivery system to work, one of the opioids should have both rapid transfer from the lungs to the plasma, and rapid transfer from the plasma to the site of opioid drug effect. Fentanyl, alfentanil, sufentanil, and remifentanil all have this characteristic (rapid onset). It may be that meperidine and methadone also have this effect, but that is not presently known. Although it is possible to obtain the required parameters of the invention with a single opioid, we have found that combining the rapid onset opioid with a slower acting, but sustained effect opioid gives a preferred result, as the patient typically feels analgesic effect for longer periods of time with such a combination.

If the desire is to maintain the opioid analgesic effect, then it may be necessary to combine the rapid onset opioid with an opioid that has a slower onset, but sustained effect. Examples of such formulations include (1) a formulation of fentanyl and liposomal encapsulated fentanyl, (2) a formulation of remifentanil, alfentanil, sufentanil, or fentanyl in combination with morphine, and (3) a formulation of remifentanil, alfentanil, sufentanil, or fentanyl in combination with methadone. Care must be taken to prevent a second "peak" of action, at the time of maximum effect of the sustained effect opioid, that is higher than the peak caused by the rapid onset opioid, which allows the patient to feel side effects while he or she is administering the drug.

When a rapid onset opioid is combined with an opioid with slow onset and sustained effect, the concentration of both opioids is adjusted so that the self-limiting effects of the rapid-onset opioid serves to limit exposure of the patient to the slow-onset opioid. The rapid onset opioid acts as an early warning system of sorts, triggering side effects in an adequate timeframe.

We have found that side effects are experienced before toxicity is reached. More specifically, subjects that experienced side effects at the end of dosing or shortly after completion of dosing did not progress to toxic side effects whereas subjects that experienced side effects during dosing and continued or were coached to continue to inhale drug progressed to toxicity, specifically, hypoxia.

As can be appreciated by the above description, creation of the invention requires (1) thorough understanding of the pharmacokinetics and pharmacodynamics of one or more opioids, and (2) thorough understanding of the relationship between opioids, carbon dioxide production and elimination, and ventilation, (3) careful selection of one or more opioids, and (4) precise determination of the optimal concentration of each opioid in the final formulation in order to achieve the desired clinical profile of the drug. The final formulation is determined by pharmacokinetic and pharmacodynamic modeling of the system parameters, with dose optimization performed to find the dose that exhibits the best patient safety profile while still providing an adequate analgesic response.

IN THE DRAWINGS

FIG. 1 is a flow diagram which represents a computer simulation model for sedation. In all flow diagrams, squares represent amounts, arrows represent rates (amounts per unit time), and circles represent either a calculation, rate, or constant.

FIG. 2 is a flow diagram which represents a computer simulation model for ventilatory depression.

FIG. 3 is a flow diagram which represents a computer simulation model for an inhalation device.

FIG. 4 is a flow diagram which represents a computer simulation model for the pharmacokinetic profiling of opioid as administered to a patient through a pulmonary route.

FIGS. 5A and 5B, taken together, are a flow diagram which represents the Stella™ computer simulation of the pharmacokinetics of the administration of a single opioid. FIG. 5A shows the Device Model and the Pharmacokinetic Model aspects of the simulation, FIG. 5B shows the Ventilatory Depression Model and the Sedation Model aspects of the simulation.

Figure 7:
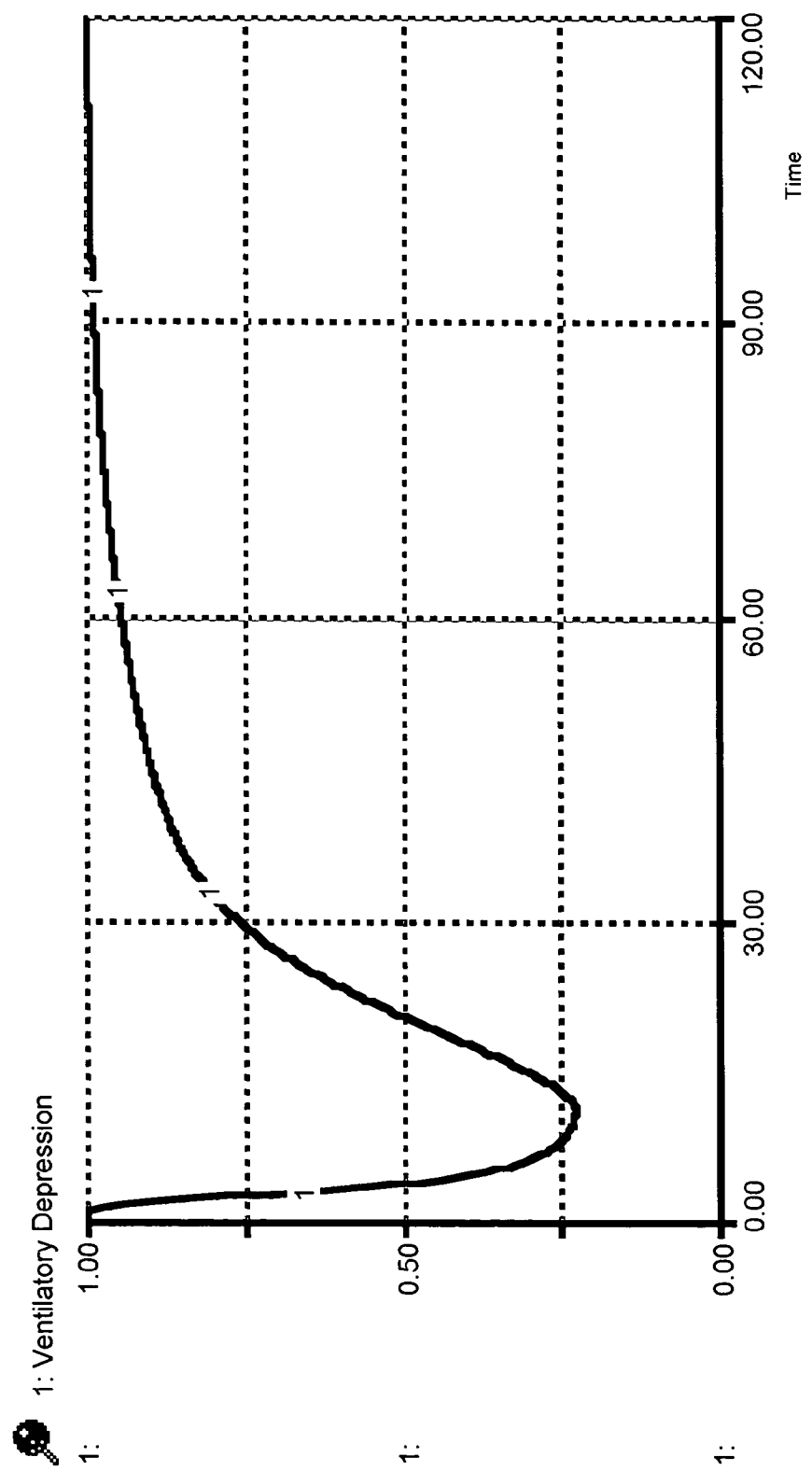
FIG. 7 is a graph showing the time course of ventilatory depression in the Stella™ computer simulation of FIGS. 5A and 5B (ventilatory depression and sedation models disabled).

FIG. 6 is a graph showing output of the STELLA® computer simulation of FIGS. 5A and 5B (ventilatory depression and sedation models disabled) expressed as a time course of quantity of opioid in the inhalation device, and quantity of opioid in the lung of the patient. The X axis shows time in minutes. The Y axis shows dose units of formulation, in mcg. The amount of drug in the inhaler dropped steadily over the first 10 minutes of stimulation. The amount of drug in the lungs reflects the net processes of inhalation of drug into the lungs and absorbtion of drug from the lungs into the systemic circulation FIG. 7 is a graph showing the time course of ventilatory depression in the STELLA® computer simulation of FIGS. 5A and 5B (ventilatory depression and sedation models disabled). Ventilatory depression (expressed as a fraction of baseline ventilation) was expressed over time of simulation (in minutes).

Figure 8:
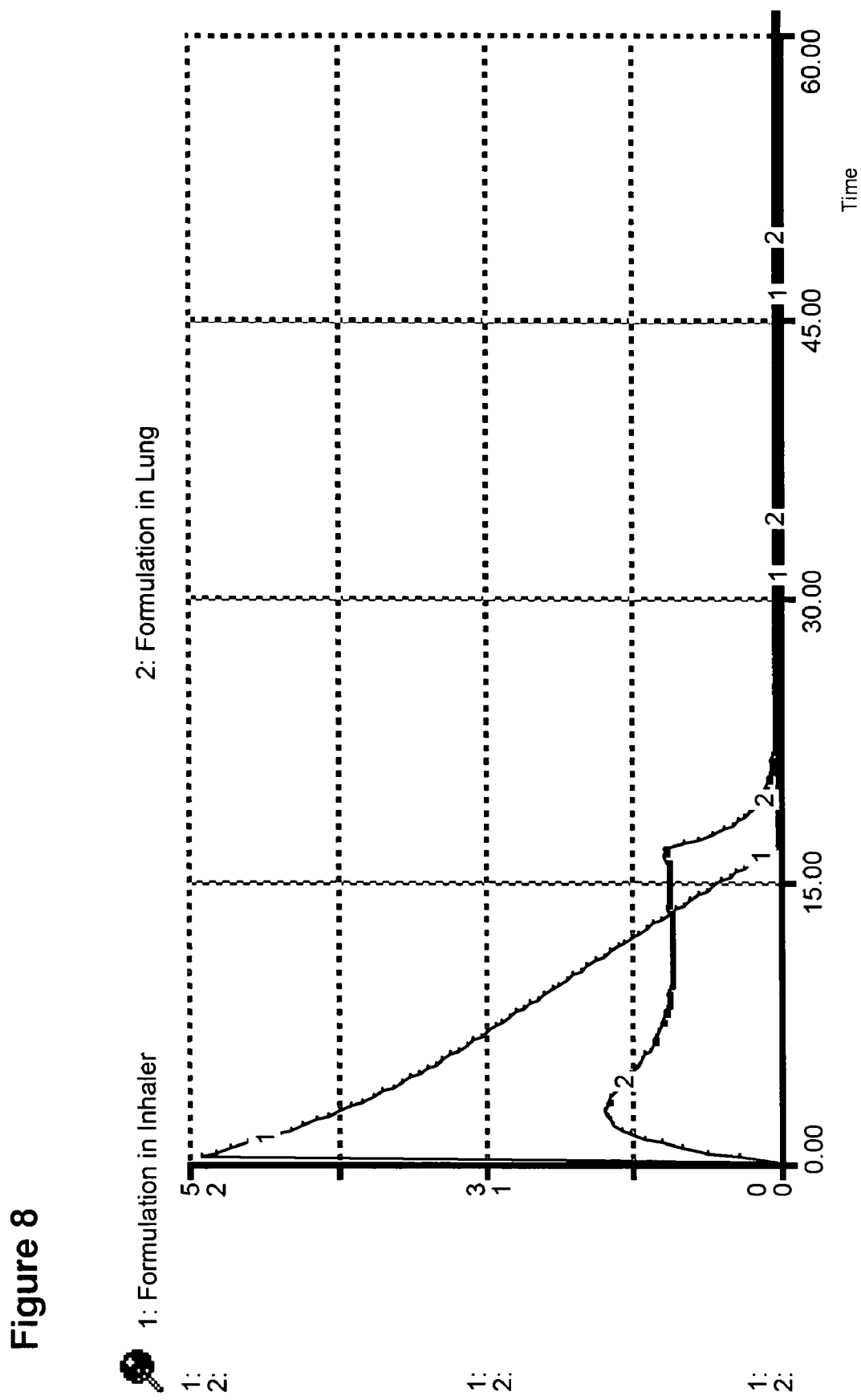
FIG. 8 is a graph showing the time course of quantity of opioid in the inhalation device and in the lung of the patient, in the Stella™ computer simulation of FIGS. 5A and 5B (ventilatory depression model enabled, sedation model disabled).

FIG. 8 is a graph showing the time course of quantity of opioid in the inhalation device and in the lung of the patient, in the STELLA® computer simulation of FIGS. 5A and 5B (ventilatory depression model enabled, sedation model disabled). The X axis shows time in minutes. The Y axis shows dose units of formulation, in mg. Patient ventilation dropped to approximately 25% of baseline ventilation, such depression persisting for approximately 5-10 minutes.

Figure 9:
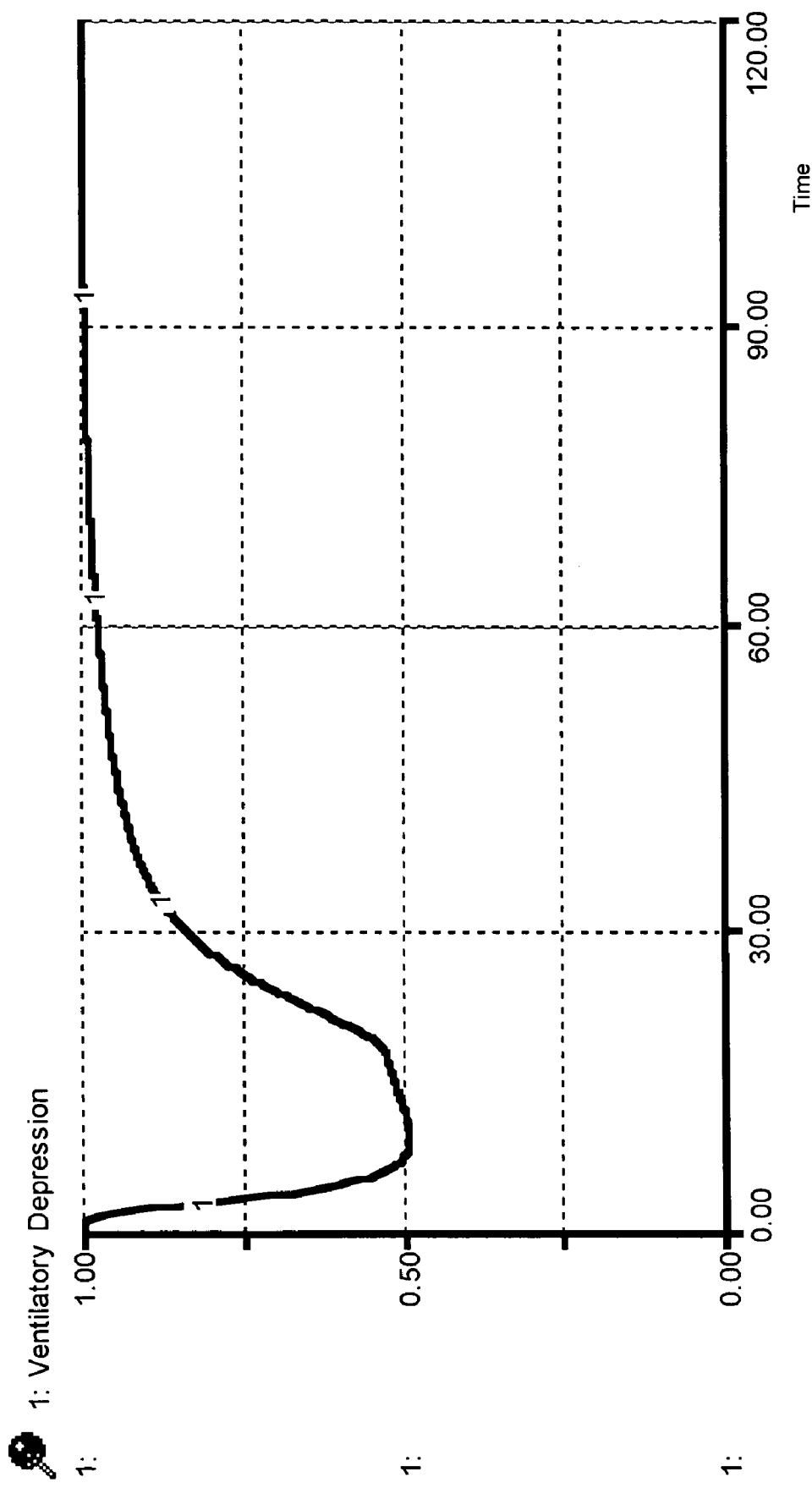
FIG. 9 is a graph showing the time course of ventilatory depression in the Stella™ computer simulation of FIGS. 5A and 5B (ventilatory depression model enabled, sedation model disabled).

FIG. 9 is a graph showing the time course of ventilatory depression in the STELLA® computer simulation of FIGS. 5A and SB (ventilatory depression model enabled, sedation model disabled). Ventilatory depression (expressed as a fraction of baseline ventilation) was expressed over time of simulation (in minutes). Change in ventilation caused by the self-limitation of opioid uptake offers considerable safety to the patient (compared to FIG. 7).

Figure 10:
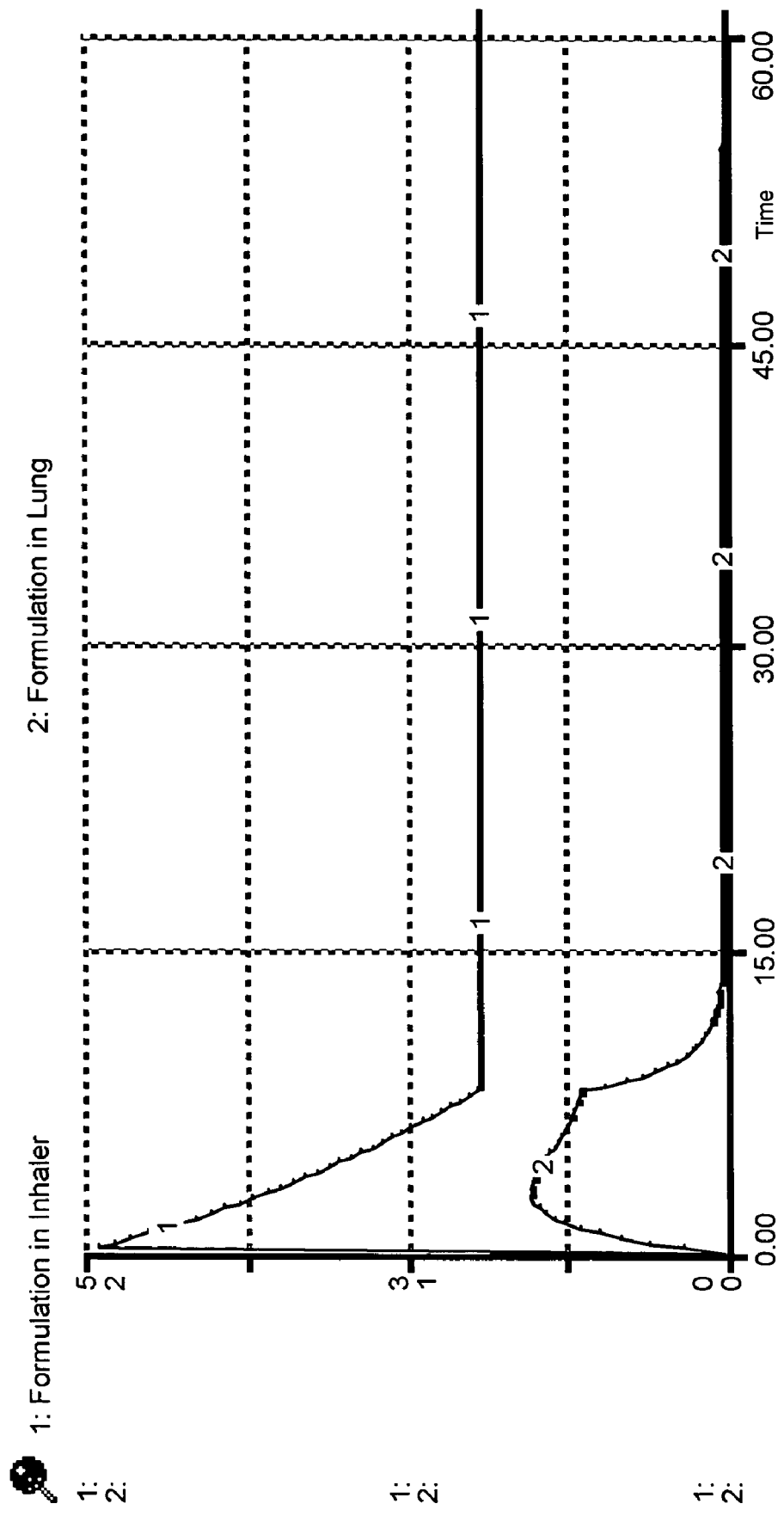
FIG. 10 is a graph showing the time course of quantity of opioid in the inhalation device and in the lung of the patient, in the Stella™ computer simulation of FIGS. 5A and 5B (ventilatory depression and sedation models enabled).

FIG. 10 is a graph showing the time course of quantity of opioid in the inhalation device and in the lung of the patient, in the Stella™ computer simulation of FIGS. 5A and 5B (ventilatory depression and sedation models enabled). The X axis shows time in minutes. The Y axis shows dose units of formulation, in mg. Drug inhalation stopped completely at approximately 8 minutes, due to a sedation state being reached and self-limitation of drug intake.

Figure 11:
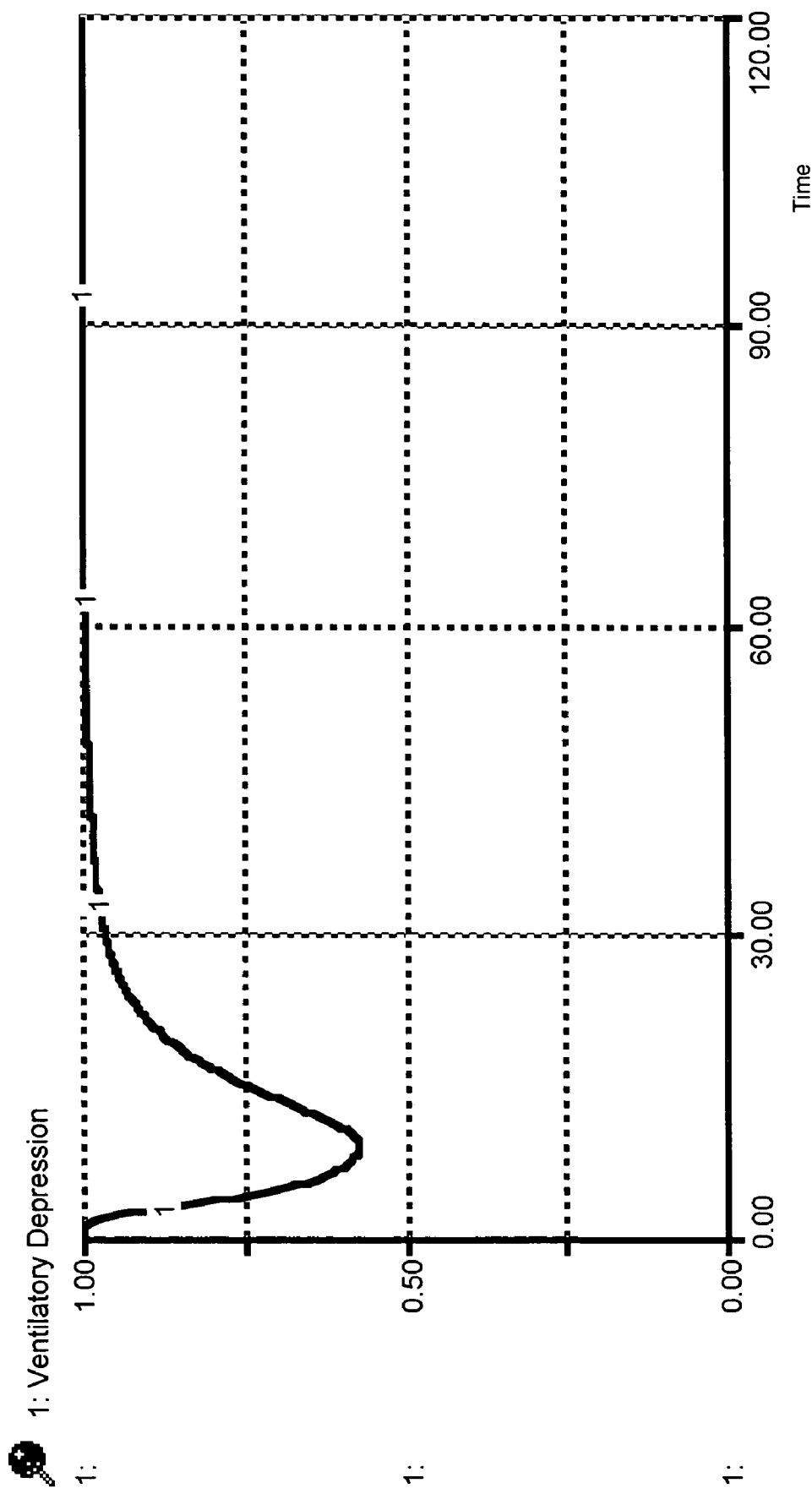
FIG. 11 is a graph showing the time course of ventilatory depression in the Stella™ computer simulation of FIGS. 5A and 5B (ventilatory depression and sedation models enabled).

FIG. 11 is a graph showing the time course of ventilatory depression in the Stella™ computer simulation of FIGS. 5A and 5B (ventilatory depression and sedation models enabled). Ventilatory depression (expressed as a fraction of baseline ventilation) was expressed over time of simulation (in minutes). Change in ventilation caused by the self-limitation of opioid uptake from sedation offers considerable safety to the patient (compared to FIG. 7 or 9).

FIG. 12 is a flow diagram which represents a computer simulation model for the administration of two opioids.

FIGS. 13A, 13B and 13C, taken together, are a flow diagram which represents the STELLA® computer simulation of the pharmacokinetics of the administration of two opioids.

FIG. 14 is a graph showing the output of Stella™ computer simulation of FIGS. 13A, 13B and 13C expressed as a time course of total quantity of opioid in the inhalation device and in the lung of the patient (ventilatory depression and sedation models enabled). Y axis shows fentanyl equivalents of formulation in the inhaler (1), of the rapid-onset opioid in the lung (2), and the sustained-effect opioid in the lung (3), expressed in ng/ml (fentanyl equivalents) of drug over time (in minutes). After approximately 12 minutes, the patient stopped inhaling more opioid, reflecting opioid-induced sedation.

FIG. 15 is a graph showing the time course of concentration of each opioid and of total opioid at the effect site in the Stella™ computer simulation of FIGS. 13A, 13B and 13C (ventilatory depression and sedation models enabled). Amount of rapid-onset opioid (1), sustained-effect opioid (2) and the combination effect of both the rapid-onset opioid and the sustained-effect opioid (3) at the site of effect were shown, in ng/ml of fentanyl equivalents, overtime (in minutes).

FIG. 16 is a graph showing the time course of ventilatory depression during and after delivery of opioids in the Stella™ computer simulation of FIGS. 13A, 13B and 13C (ventilatory depression and sedation models enabled). Ventilatory depression (expressed as a fraction of baseline ventilation) was expressed over time of simulation (in minutes). The combination of the two opioids reaches a peak during the administration of the first opioid.

FIGS. 17A, 17B and 17C, taken together, are a flow diagram which represents the Stella™ computer simulation of the pharmacokinetics of the administration of two opioids, where the two opioids being administered are alfentanil and morphine. FIGS. 17A and 17B show the Device Model and the Pharmacokinetic Model aspects of the simulation, while FIG. 17C shows the Ventilatory Depression Model, the Sedation Model, and the Two Drug Model aspects of the simulation.

FIG. 18 is a graph showing the time course of concentration of alfentanil, morphine, and combined opioid at the effect site in the Stella™ computer simulation of FIGS. 17A, 17B and 17C (ventilatory depression and sedation models enabled). Line 1 shows concentration of alfentanil; line 2 shows concentration of morphine, and line 3 shows combined concentration. All drug levels are shown at the site of effect, and expressed in ng/ml of fentanyl equivalents over time (in minutes). Drug administration was terminated after delivery of 90% of the drug because of patient sedation. As seen in line 3, the highest opioid exposure occurs during inhalation.

Figure 19:
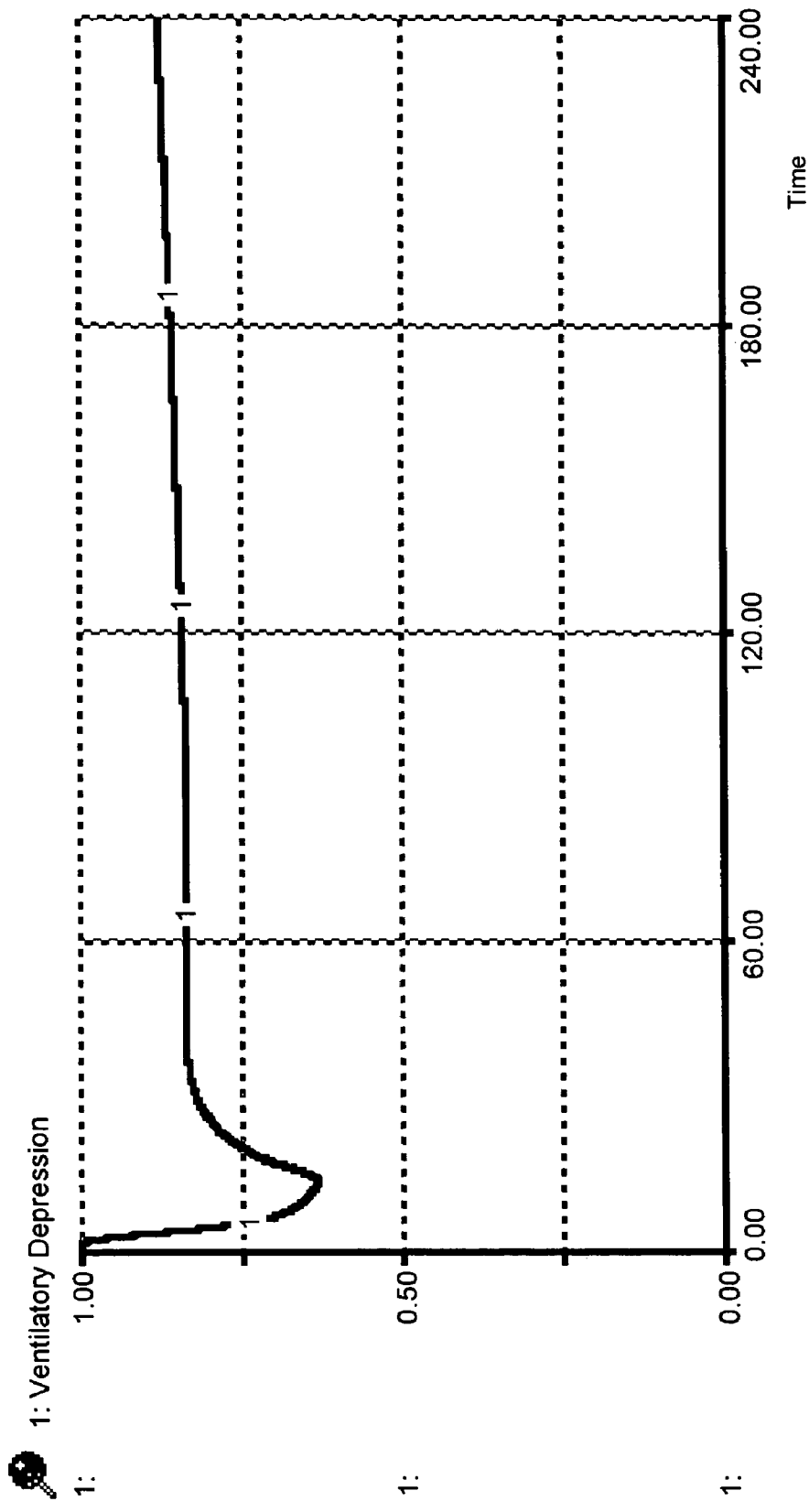
FIG. 19 is a graph showing the time course of ventilatory depression in the Stella™ computer simulation of FIGS. 17A, 17B and 17C (ventilatory depression and sedation models enabled).

FIG. 19 is a graph showing the time course of ventilatory depression in the Stella™ computer simulation of FIGS. 17A, 17B and 17C (ventilatory depression and sedation models enabled). Ventilatory depression (expressed as a fraction of baseline ventilation) was expressed over time of simulation (in minutes). Ventilation decreases to about 65% of baseline during drug administration.

Figure 20A:
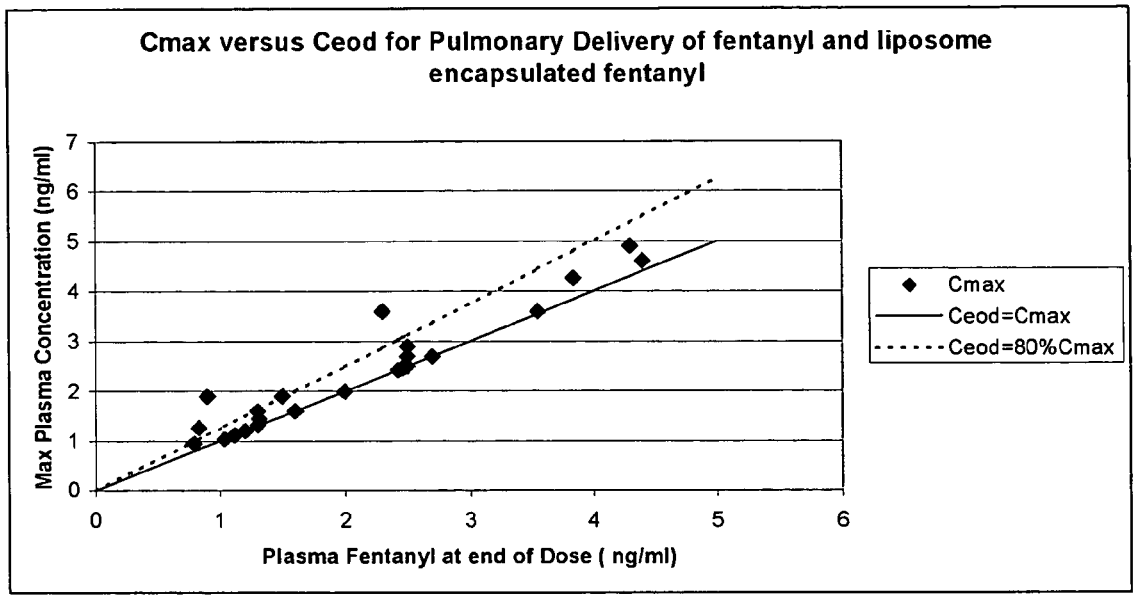
FIG. 20A shows patients administered with a combination of fentanyl and liposomally encapsulated fentanyl through a pulmonary route.
Figure 20B:
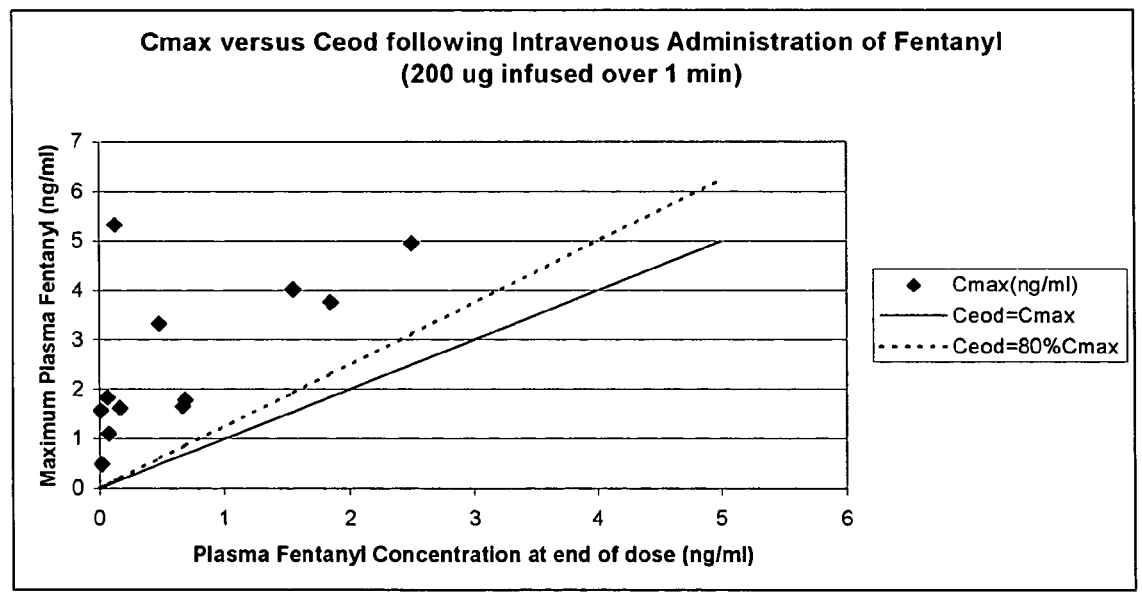
FIG. 20B shows patients administered with fentanyl intravenously.

FIG. 20 is a graph showing maximum concentration of opioid in the plasma against end of dose concentration of opioid in the plasma of patients administered opioid. FIG. 20A shows patients administered with a combination of fentanyl and liposomally encapsulated fentanyl through a pulmonary route. FIG. 20B shows patients administered with fentanyl intravenously. Maximum concentration of opioid was not significantly higher than the concentration at end of dose, indicating that if the "end of dose" amount is non-toxic, the maximum concentration of opioid taken by the subject is likely also non-toxic.

Figure 21:
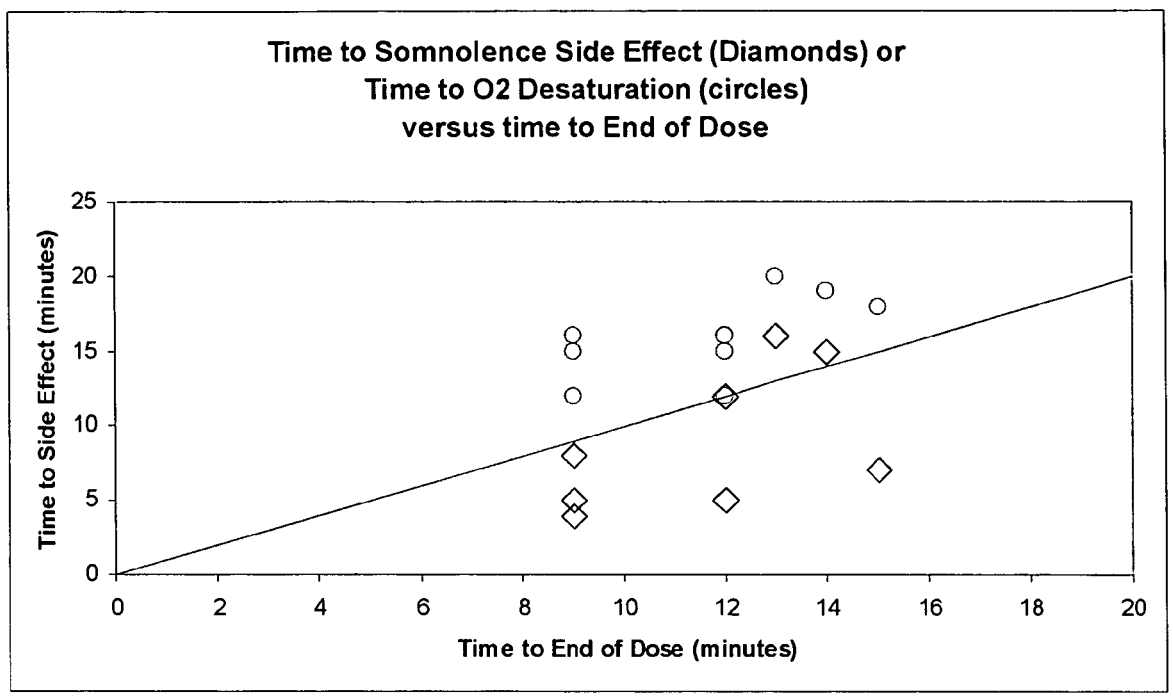
FIG. 21 is a graph showing time to side/toxic effect versus time to end of dose for the side effects and toxic effects of patients administered a combination of fentanyl and liposomally encapsulated fentanyl through a pulmonary route.

FIG. 21 is a graph showing time to side/toxic effect versus time to end of dose for the side effects and toxic effects of patients administered a combination of fentanyl and liposomally encapsulated fentanyl through a pulmonary route. In all cases, time to toxicity was equal to or longer than time to side effect.

FIG. 22 is a table showing the statistical correlation of side effect to toxic effect. Side effect is correlated to toxic effect at a $p<.04$.

EXAMPLES

The examples below are designed to demonstrate but not limit the embodiments of the present invention.

Example 1

Theoretical Model for Opioid Delivery

Examples 2-4 are based on a theoretical model for opioid delivery; this theoretical model is described for greater certainty here in Example 1.

The theoretical model for opioid delivery was programmed into the computer simulation package STELLA® (High Performance Systems, Lebanon, N.H.). The elements shown in this example, both in figures and in text, are adapted from the STELLA® model representation, and explain both the programming of the simulation, and how the simulation works.

In the figures, rectangles represent variables that indicate accumulation of a substance (with exceptions noted below). Open arrows represent flow into or out of the accumulators, and closed arrows represent the elements that control the flow. Some closed arrows are omitted for simplicity of representation. Ovals represent model parameters (inputs) and time-independent calculations. Many model parameters and constants were obtained from the prior art (see Scott J C, Stanski D R Decreased fentanyl and alfentanil dose requirements with age. A simultaneous pharmacokinetic and pharmacodynamic evaluation. J Pharmacol Exp Ther. 1987 Jan;240(1): 159-66).

(a) Sedation Model

A model for opioid induced sedation was designed (FIG. 1—Sedation Model). Opioid in Effect Site 1010 was used as a variable denoting the concentration of opioid at the site of drug effect. If more than 1 opioid was present at the site of drug effect, Opioid in Effect Site 1010 was built to represent the sum of the opioids present, each normalized to their relative potency (for example, in Examples 3 and 4, below).

[Sedation Threshold 1020 was defined as the Opioid Concentration 1010 that would render the patient unable to use the inhaler. Sedation Threshold 1020 was determined either through experimentation or through the known pharmacokinetics of the opioid.

Sedation Evaluator 1030 was a test of whether Opioid Concentration 1010 exceeded Sedation Threshold 1020. If Opioid Concentration 1010 exceeded Sedation Threshold 1020, Sedation Evaluator converted the value of Sedation State 1040 from 0 to 1. Sedation State 1040 was an exception to the rule that rectangles represent accumulation of a substance: Instead, the role of Sedation State 1040 within the model was that of a memory component, which would remember that the opioid had exceeded the sedation threshold. In subsequent models, data from Sedation State 1040 functioned to turn off further administration of opioids, simulating patient sedation and the resulting removal of the inhaler from the mouth.

(b) Ventilatory Depression Model

A Ventilatory Depression simulation was programmed (FIG. 2). In this model, $CO_2$ was produced by the metabolic activity of the body at a rate $CO_2$ Production 2010, flowed into the plasma, (Plasma $CO_2$ 2020). $CO_2$ Production 2010 was either determined experimentally, or known from prior art (see, for example, Bouillon T, Schmidt C, Garstka G, Heimbach D, Stafforst D, Schwilden H, Hoeft A. Pharmacokinetic-pharmacodynamic modeling of the respiratory depressant effect of alfentanil. Anesthesiology. 1999 July;91 (1):144-55 and Bouillon T, Bruhn J, Radu-Radulescu L, Andresen C, Cohane C, Shafer S L. A model of the ventilatory depressant potency of remifentanil in the non-steady state. Anesthesiology. 2003 October;99(4):779-87.). Plasma CO2 2020 equilibrated with the CO2 in the brain (Brain CO2 2040) at a rate (Brain-Plasma CO2 Equilibrium 2030). CO2 was eliminated from the plasma in a manner simulating the exhalation of air from the lungs, at a rate CO2 Elimination 2050 that was mediated by the parameter Ventilatory Depression 2060.

Ventilatory Depression 2060 increased as the opioid concentration at the site of drug effect (Opioid in Effect Site 1010) increased. Ventilatory Depression decreased the elimination of CO2 from the lungs (CO2 Elimination 2050), causing CO2 to rise in the brain, (Brain CO2 2040). As Brain CO2 2040 increased, it stimulated ventilation through a negative effect on Ventilatory Depression 2060, offsetting in part the depressant effects of Opioid in Effect Site 1010, which has a positive effect on Ventilatory Depression 2060.

Other parameters were designed to effect Ventilatory Depression 2060; the sum of these parameters were illustrated in this model as Model Parameters 2070; parameters comprising Model Parameters 2070 were described in greater detail in FIGS. 5A and 5B. These Model Parameters 2070 effect Ventilatory Depression 2060, which in turn effects CO2 Elimination 2050 and Brain CO2 2040.

Although the programming of this simulation into the STELLA® computer simulation model is novel, the Ventilatory Depression Model is known in the art, and is referred to as an "Indirect Response Model."

(c) Device Model

A model for the inhalation device is shown in FIG. 3. Dose 3050 represents the total amount of opioid added to the Inhaler. Opioid Dose 3050 is added to the inhaler at a rate Fill Inhaler 3010. This rate is required for the working of the simulation, but is calculated at an instantaneous rate. Formulation In Inhaler 3020 represents the opioid contained within the inhaler. The patient inhales the formulation at a rate of inhalation (Inhalation 3030) into the lungs, (Formulation in Lungs 3040). Inhalation 3030 is effected by Ventilatory Depression 2060 and Sedation State 1040. Specifically, Inhalation 3030 is slowed by the increase of Ventilatory Depression 2060. For example, if Ventilatory Depression 2060 was 50% of baseline, then drug was inhaled at half the baseline rate (Inhalation 3030 was half baseline). However, if Sedation State 1040=1, then inhalation of drug into the lungs ends, and no further drug is inhaled.

(d) Pharmacokinetic Model

A Pharmacokinetic Model for systemic opioid was programmed. Formulation In Lungs 3040 was absorbed systemically at a rate Systemic Absorption 4010 into the blood plasma (Opioid in Plasma 4020). Opioid in Plasma 4020 equilibrated at a rate Plasma-Effect Site Drug Equilibrium 4030 with opioid at the site of drug effect (Opioid in Effect Site 1010). Opioid also redistributed into tissue Opioid in Tissue 4060 at a rate Opioid Redistribution 4050 or was eliminated from the plasma at a rate Opioid Elimination 4070. Opioid in Tissue 4060 and Opioid Redistribution 4050 were programmed as optional parameters that could be used or not used depending on the pharmacokinetic model of the particular opioid utilized. The rates Systemic Absorption 4010, Plasma-Effect Site Drug Equilibrium 4030, Opioid Elimination 4070, and Opioid Redistribution 4050 were all determined by a vector of pharmacokinetic parameters of the particular opioid being administered, represented in the model as Opioid Pharmacokinetic Parameters 4080, and calculated by pharmacokinetic modeling.

Although the programming of this simulation into Stella was novel, the Pharmacokinetic Model is known in the art, and is referred to as a "Mammillary Pharmacokinetic Model With An Effect Site." Mammillary models as represented above typically have 0, 1 or 2 tissue compartments, yielding models referred to as 1, 2, or 3 Compartment Models with an effect site, respectively.

Example 2

Administration of a Single Opioid

This example is an application of Example 1: Theoretical Model for Opioid Delivery. This example is meant to illustrate the Theoretical Model for Opioid Delivery in use; the model parameters do not reflect any specific opioid. Instead, the model parameters in this example have been designed to clearly demonstrate the self-limiting aspect of the proposed system of opioid delivery. This Example shows the integration of the four simulations as described in Example 1, and output from the model when the simulation is run.

(a) Integration of the Model

FIGS. 5A and 5B show the elements of the model as described in Example 1, wherein a single opioid is administered through inhalation. FIG. 5 is split into two parts: FIG. 5A and FIG. 5B. FIG. 5A encompasses: a Device Model 5010 that is equivalent to the Device Model shown and explained in Example 1 as the whole of FIG. 3; a Pharmacokinetic Model 5020 that is equivalent to the Pharmacokinetic Model shown and explained in Example 1 as the whole of FIG. 4 (with the exception of the exclusion of optional parameters Opioid in Tissue 4060 and Opioid Redistribution 4050, and with the further exception that Opioid Pharmacokinetic Parameters 4080 were built into Systemic Absorbtion 4010, Opioid Elimination 4070, and Plasma Effect Site Equilibration 4030, and not shown as a separate parameter—see source code for more information): FIG. 5B encompasses: a Ventilatory Depression Model 5030, which was equivalent to the Ventilatory Depression Model shown and explained in Example 1 as the whole of FIG. 2 (with the exception that Model Parameters 2070 are shown in 'expanded' form, with various elements comprising Model Parameters 2070, namely PACO2@0 2071, KelCO2 2072, ke0CO2 2073, C50 2074, Gamma 2075, and F 2076, shown; and a Sedation Model 5040, that is equivalent to the Sedation Model shown in FIG. 1. The Models shown in FIGS. 5A and 5B are part of the same simulation, but are shown in two figures for ease of reference. The mechanics of the four models, shown in FIGS. 5A and 5B, were described in depth in Example 1, with the exception of the expansion of Model Parameters 2070, the mechanics of which are explained as follows:

Baseline CO2 2071 is the CO2 at baseline, prior to administration of opioid. kel CO2 2072 is the elimination rate relating Plasma CO2 2020 to CO2 Elimination 2050, so that at baseline (i.e., in the absence of ventilatory depression):

$$\text{CO2 Elimination } 2050 = \text{kel CO2 } 2072 \times \text{Plasma CO2 } 2020$$

It follows that at baseline, carbon dioxide in the body is at steady state, and hence the CO2 Elimination 2050=CO2 Production 2010. This permits calculation of the rate of CO2 production (which is constant) in terms of Baseline CO2 2071 and kel CO2 2072 as:

CO2 Production 2010=kel CO2 2072×Baseline Plasma CO2 2071

The rate of Brain Plasma Equilibration 2020 is determined by the parameter keO CO2 2073, so that:

Brain Plasma Equilibration 2020=ke0 CO2 2073× (Plasma CO2 2020–Brain CO2 2040)

Opioids depress ventilation as a sigmoidal function of the Opioid in the Effect Site, 1030, and the parameters C50 2074, the opioid concentration associated with 50% of maximum effect, and gamma 2075, the steepness of the concentration vs. response relationship, with the contribution of the opioid to ventilatory depression expressed as:

$$1 - \frac{\text{Opioid in the effect site } 1030^{gamma\,2075}}{C50\,2074^{gamma\,2075} + \text{Opioid in the effect site } 1030^{gamma\,2075}}$$

Conversely, carbon dioxide stimulations ventilation. The increase in ventilation can be modeled as a function of Baseline CO2 2071, Brain CO2 2040, and F 2076, a parameter describing the steepness of the relationship:

$$\left(\frac{\text{Brain } CO2\,2040}{\text{Baseline } CO2\,2071}\right)^{F\,2076}$$

Putting these together, Ventilatory Depression 2060 can be described as:

$$\text{Ventilatory depression } 2060 = \left(1 - \frac{\text{Opioid in the effect site } 1030^{gamma\,2075}}{C50\,2074^{gamma\,2075} + \text{Opioid in the effect site } 1030^{gamma\,2075}}\right) \times \left(\frac{\text{Brain } CO2\,2040}{\text{Baseline } CO2\,2071}\right)^{F\,2076}$$

With ventilatory depression 2060 now defined, we can fully define CO2 Elimination 2050 in the presence of opioid induced ventilatory depression as:

CO2 Elimination 2050=kel CO2 2072×Plasma CO2 2020×Ventilatory Depression 2060 completing the description of the model.

In this manner, the models from Example 1 were combined into one model of opioid effect. This model, shown in FIGS. 5A and 5B, can also be described by the following mathematical model, as represented in the Stella programming language (source code):

```
Brain_CO2_2040(t)        =       Brain_CO2_2040(t    –    dt)    +
(Brain_Plasma_CO2_Equilibration_2020) * dt
INIT Brain_CO2_2040 = Baseline_CO2_2071
INFLOWS:
Brain_Plasma_CO2_Equilibration_2020                             =
ke0_CO2_2073*(Plasma_CO2_2020–Brain_CO2_2040)
Formulation_in_Inhaler_3020(t)                                  =
Formulation_in_Inhaler_3020(t – dt) + (Fill_Inhaler_3010         –
Inhalation_3030) * dt
INIT Formulation_in_Inhaler_3020 = 0
INFLOWS:
Fill_Inhaler_3010 = if time = 0 then Dose_3050/DT else 0
OUTFLOWS:
Inhalation_3030   =   If Sedation_State_1040   =   0   then
.5*(Ventilatory_Depression_2060) else 0
Formulation_in_Lung_3040(t) = Formulation_in_Lung_3040 (t        –
dt) + (Inhalation_3030 – Systemic_Absorption_4010) * dt
INIT Formulation_in_Lung_3040 = 0
INFLOWS:
Inhalation_3030   =   If Sedation_State_1040   =   0   then
.5*(Ventilatory_Depression_2060) else 0
OUTFLOWS:
Systemic_Absorption_4010 = Formulation_in_Lung_3040*.693/1
Opioid_in_Effect_Site_1010(t)                                   =
Opioid_in_Effect_Site_1010(t       –          dt)               +
(Plasma_Effect_Site_Equilibration_4030) * dt
INIT Opioid_in_Effect_Site_1010 = 0
INFLOWS:
Plasma_Effect_Site_Equilibration_4030                           =
(Opioid_in_Plasma_4020–Opioid_in_Effect_Site_1010)*.693/1
Opioid_in_Plasma_4020(t) = Opioid_in_Plasma_4020(t – dt)         +
(Systemic_Absorption_4010    –    Opioid_Elimination_4070        –
Plasma_Effect_Site_Equilibration_4030) * dt
INIT Opioid_in_Plasma_4020 = 0
INFLOWS:
Systemic_Absorption_4010 = Formulation_in_Lung_3040*.693/1
OUTFLOWS:
Opioid_Elimination_4070 = Opioid_in_Plasma_4020*.693/10
Plasma_Effect_Site_Equilibration_4030                           =
(Opioid_in_Plasma_4020–Opioid_in_Effect_Site_1010)*.693/1
```

-continued

```
Plasma_CO2_2020(t)    =   Plasma_CO2_2020(t  -   dt)                +
(CO2_Production_2010 - Brain_Plasma_CO2_Equilibration_2020
- CO2_Elimination_2050) * dt
INIT Plasma_CO2_2020 = Baseline_CO2_2071
INFLOWS:
CO2_Production_2010 = Baseline_CO2_2071*kelCO2_2072
OUTFLOWS:
Brain_Plasma_CO2_Equilibration_2020                                 =
ke0_CO2_2073*(Plasma_CO2_2020 - Brain_CO2_2040)
CO2_Elimination_2050                                                =
Plasma_CO2_2020*kelCO2_2072*Ventilatory_Depression_2060
Sedation_State_1040(t) = Sedation_State_1040(t   -   dt)            +
(Sedation_Evaluator_1030) * dt
INIT Sedation_State_1040 = 0
INFLOWS:
Sedation_Evaluator_1030                                             =
if(Opioid_in_Effect_Site_1010>Sedation_Threshhold_1020)
then 1 else 0
Baseline_CO2_2071 = 40
C50_2074 = .3
Dose_3050 = 5
F_2076 = 4
Gamma_2075 = 1.2
ke0_CO2_2073 = 0.92
kelCO2_2072 = 0.082
Sedation_Threshhold_1020 = 1.5
Ventilatory_Depression_2060=                                        (1-
Opioid_in_Effect_Site_1010^Gamma_2075/ (C50_2074^Gamma_2075+
Opioid_in_Effect_Site_1010^Gamma_2075) )*(Brain_CO2_2040/Base-
line_CO2_2071)^F_2076
```

(b) Output of the Model when Run with Ventilatory Depression Model and Sedation Model Disabled The model designed and described in (a) was run as a simulation of opioid effect, using the following initial parameters: Formulation In Inhaler 3020=5 milliliters at time=0. The model was allowed to run over a time course of two hours. For this simulation, the feedback loop on drug uptake aspects of the Ventilatory Depression Model (i.e. the feedback of the effect of Ventilatory Depression 2060 on Device Model 5010), and the Sedation Model were disabled. Output of the model, when run, was plotted for various parameters in FIGS. 6 and 7.

FIG. 6 shows the output of the model as run in the absence of patient self-limiting inhalation of opioid (i.e. with the Ventilatory Depression Model and the Sedation Model disabled). FIG. 6 shows the time course of drug in the inhaler (Formulation In Inhaler 3020—line 1), and in the lungs (Formulation in Lungs 3040—line 2) in the absence of the self-limiting aspects of the invention. The amount of drug in the inhaler dropped steadily over the first 10 minutes of simulation, at a rate Inhalation 3030. The amount of drug in the lungs reflected the net processes of inhalation of drug into the lungs, and absorption of drug from the lungs into the systemic circulation.

FIG. 7 shows Ventilatory Depression 2060 over time, for the same simulation (Ventilatory Depression Model and Sedation Model disabled). The graph output indicated that patient's ventilation dropped to approximately 25% of baseline ventilation in this simulation. The ventilatory depression persisted for approximately 5-10 minutes. The drop in ventilation was reversed as carbon dioxide built up in the patient's plasma, and, at the same rate, the patient's lungs (not simulated), counteracting the depressant effect of the opioid on ventilation. This drop in ventilation exposed the patient to risk from injury from hypoxia.

(c) Output of the Model when Run with Ventilatory Depression Model Enabled

The simulation used in (b) was modified by enabling the Ventilatory Depression Model, and run again with the same initial parameters of Formulation In Inhaler 3020=5 milliliters at time 0. Output of various parameters were plotted over time. FIG. 8 shows Formulation In Inhaler 3020 (line 1), depicting the amount of drug that is left in the inhaler, and Formulation In Lungs 3040 (line 2), depicting the amount of drug in the lungs, in the presence of ventilatory depression, one of the two self-limiting aspects of the invention (the other being sedation). As compared to Example 2(b), as expected, it took longer to inhale the drug when the simulation was run with the Ventilatory Depression Model enabled—inhalation of drug in FIG. 8 took place over approximately 17 minutes as opposed to the 10 minutes in FIG. 6. This was due to a reduction in ventilation caused by ventilatory depression, which limited the patient's exposure to the opioid. This reduction in ventilation was best illustrated in FIG. 9, which plotted Ventilatory Depression 2060 over time for the same simulation. Ventilatory Depression 2060 was depressed by 50% in FIG. 9. When compared with the simulation shown in FIG. 7, the patient was breathing half as much (in FIG. 9) as when simulation was run with the Ventilatory Depression Model deactivated (in FIG. 7). This simulation shows that the change in ventilation caused by the self-limitation of opioid uptake offers considerable safety to the patient.

(d) Output of the Model when Run with Ventilatory Depression Model and Sedation Model Enabled The same simulation (Formulation In Inhaler 3020=5 milliliters at time=0) was run, this time with both the Ventilatory Depression Model 5030 and the Sedation Model 5040 enabled. Output of various parameters were plotted, over time. FIG. 10 shows the time course of Formulation In Inhaler 3020 (Line 1) and Formulation In Lungs 3040 (Line 2) in the presence of ventilatory depression and sedation. As seen in the figure, after 8 minutes drug inhalation stopped completely. The reason was that the patient has become sedated, and could no longer hold the inhaler to the mouth (simulated here as Sedation State 1040 turning from 0 to 1). At this time, approximately 2 milliliters remained in Formulation In Inhaler 3020, and therefore, approximately 40% of the opioid dose remained in the inhaler and was not inhaled. FIG. 11 plots Ventilatory Depression 2060 during the time course of this simulation. The maximum depression of ventilation in FIG. 11 was approximately 60%. When compared with FIG. 9, the improved safety from the opioid-induced sedation is evident.

Thus, Example 2, as illustrated in FIGS. 5 through 11, demonstrate through simulation the effects and advantages of the self-limiting system of opioid delivery, as described herein.

Example 3

Administration of Two Opioids

In this simulation, the model parameters do not reflect any specific opioids, but have been adjusted to demonstrate clearly the self-limiting aspect of the proposed system of opioid delivery. The simulation models and measures the same variables, this time for an opioid composition comprising of two different opioids with different pharmacokinetics.

(a) Building a Two Opioid Model.

FIG. 12 addresses how two opioids are combined into a single opioid concentration for the model. In the two opioid simulation, Rapid Opioid In Effect Site 12010 represents the concentration of rapid onset opioid; Slow Opioid In Effect Site 12020 represents the slow onset opioid. Each of these is determined in parallel and in the same manner as in the one opioid model (Example 2). However, each is determined separately, then combined to determine Combined Opioid Effect Site Concentration 12030. Combined Opioid Effect Site Concentration 12030 is calculated using the known relative potency of each opioid, Relative Potency 12040. Combined Opioid Effect Site Concentration 12030 is equal to, and depicted as, Opioid in effect Site 1010 in the two opioid models illustrated in FIGS. 13A, 13B, 13C and FIGS. 17A, 17B and 17C.

FIGS. 13A, 13B and 13C, taken together, illustrate the algorithm for the two opioid model simulation. It encompasses: a Device Model 13010, equivalent to and illustrated as Device Model 5010 and as described in Examples 1 and 2; a Pharmacokinetic Model 13020 comprising a combination of two instances of the Pharmacokinetic Model 5020 (one for the rapid opioid, and one for the slow opioid), each as illustrated in FIGS. 4, 5A and 5B, and as described in Examples 1 and 2, and each running in parallel, then combined using the Two Drug Model 13050, as described in FIG. 12; a Ventilatory Depression Model 5030, as illustrated in FIG. 2 and FIGS. 5A and 5B, and as described in Examples 1 and 2; and a Sedation Model, 5040, as illustrated in FIG. 2, FIGS. 5A and 5B, and as described in Examples 1 and 2.

The model shown in FIGS. 13A, 13B and 13C can also be described by the following mathematical model, as represented in the Stella programming language (source code).

```
Brain_CO2_2040(t)       =       Brain_CO2_2040(t   -   dt)   +
(Brain_Plasma_CO2_Equilibration_2020) * dt
INIT Brain_CO2_2040 = Baseline_CO2_2071
INFLOWS:
Brain_Plasma_CO2_Equilibration_2020                          =
ke0_CO2_2073*(Plasma_CO2_2020–Brain_CO2_2040)
Formulation_in_Inhaler_3020(t)                               =
Formulation_in_Inhaler_3020(t – dt) + (Fill_Inhaler_3010     –
Inhalation_1_3031 – Inhalation_2_3032) * dt
INIT Formulation_in_Inhaler_3020 = 0
INFLOWS:
Fill_Inhaler_3010 = if time = 0 then Dose_3050/DT else 0
OUTFLOWS:
Inhalation_1_3031   =   if Sedation_State_1040   =   0   then
0.25*Ventilatory_Depression else 0
Inhalation_2_3032   =   if Sedation_State_1040   =   0   then
0.25*Ventilatory_Depression_2060 else 0
Opioid_in_Effect_Site_1010(t)                                =
Opioid_in_Effect_Site_1010(t – dt)
INIT Opioid_in_Effect_Site_1010 = 0
Plasma_CO2_2020(t)      =       Plasma_CO2_2020(t  -   dt)   +
(CO2_Production_2010 – Brain_Plasma_CO2_Equilibration_2020
– CO2_Elimination_2050) * dt
INIT Plasma_CO2_2020 = Baseline_CO2_2071
INFLOWS:
CO2_Production_2010 = { Place right hand side of equation
here... }
OUTFLOWS:
Brain_Plasma_CO2_Equilibration_2020                          =
ke0_CO2_2073*(Plasma_CO2_2020–Brain_CO2_2040)
CO2_Elimination_2050                                         =
Plasma_CO2_2020*kelCO2_2072*Ventilatory_Depression_2060
Rapid_Drug_Effect_Site(t) = Rapid_Drug_Effect_Site(t – dt)
+ (Rapid_Drug_Plasma_Effect_Site_Equilibration) * dt
INIT Rapid_Drug_Effect_Site = 0
INFLOWS:
Rapid_Drug_Plasma_Effect_Site_Equilibration                  =
(Rapid_Drug_In_Plasma–Rapid_Drug_Effect_Site)*.693/1
Rapid_Drug_In_Plasma(t) = Rapid_Drug_In_Plasma(t – dt)       +
(Rapid_Drug_Absorption       -       Rapid_Drug_Clearance    -
Rapid_Drug_Plasma_Effect_Site_Equilibration) * dt
INIT Rapid_Drug_In_Plasma = 0
INFLOWS:
```

-continued

```
Rapid_Drug_Absorption                                                    =
Rapid_Formulation_in_Lung*.693/1*Rapid_Drug_Concentration
OUTFLOWS:
Rapid_Drug_Clearance = Rapid_Drug_In_Plasma*.693/10
Rapid_Drug_Plasma_Effect_Site_Equilibration                              =
(Rapid_Drug_In_Plasma-Rapid_Drug_Effect_Site)*.693/1
Rapid_Formulation_in_Lung(t) = Rapid_Formulation_in_Lung(t
– dt) + (Inhalation_1_3031 – Rapid_Drug_Absorption) * dt
INIT Rapid_Formulation_in_Lung = 0
INFLOWS:
Inhalation_1_3031   =   if   Sedation_State_1040   =   0   then
0.25*Ventilatory_Depression else 0
OUTFLOWS:
Rapid_Drug_Absorption                                                    =
Rapid_Formulation_in_Lung*.693/1*Rapid_Drug_Concentration
Sedation_State_1040(t)   =   Sedation_State_1040(t   –   dt)             +
(Sedation_Evaluator_1030) * dt
INIT Sedation_State_1040 = 0
INFLOWS:
Sedation_Evaluator_1030                                                  =
if (Opioid_in___Effect_Site_1010>Sedation_Threshhold_1020)
then 1 else 0
Slow_Drug_Effect_Site(t) = Slow___Drug_Effect_Site(t – dt)               +
(Slow_Drug_Plasma_Effect_Site_Equilibration) * dt
INIT Slow_Drug_Effect_Site = 0
INFLOWS:
Slow_Drug_Plasma_Effect_Site_Equilibration                               =
(Slow_Drug_In_Plasma-Slow_Drug_Effect_Site)*.693/10
Slow_Drug_In_Plasma(t)   =   Slow_Drug_In_Plasma(t   –   dt)             +
(Slow_Drug_Absorption       –       Slow_Drug_Clearance                  –
Slow_Drug_Plasma_Effect_Site_Equilibration) * dt
INIT Slow_Drug_In_Plasma = 0
INFLOWS:
Slow_Drug_Absorption                                                     =
Slow_Formulation_In_Lung*.693/12*Slow_Drug_Concentration
OUTFLOWS:
Slow_Drug_Clearance = Slow_Drug_In_Plasma*.693/300
Slow_Drug_Plasma_Effect_Site_Equilibration                               =
(Slow_Drug_In_Plasma-Slow_Drug_Effect_Site)*.693/10
Slow_Formulation_In_Lung(t) = Slow_Formulation_In_Lung(t –
dt) + (Inhalation_2_3032 – Slow_Drug_Absorption) * dt
INIT Slow_Formulation_In_Lung = 0
INFLOWS:
Inhalation_2_3032   =   if   Sedation_State_1040   =   0   then
0.25*Ventilatory_Depression_2060 else 0
OUTFLOWS:
Slow_Drug Absorption                                                     =
Slow_Formulation_In_Lung*.693/12*Slow_Drug_Concentration
Baseline_CO2_2071 = 40
C50_2074 = .3
Dose_3050 = 5
F_2076 = 4
Gamma_2075 = 1.2
ke0_CO2_2073 = 0.92
kelCO2_2072 = 0.082
Opioid_in___Effect_Site_1010                                             =
Rapid_Drug_Effect_Site+Slow_Drug_Effect_Site
Rapid_Drug Concentration = 1
Sedation_Threshhold_1020 = 1.5
Slow_Drug_Concentration = 1
Ventilatory_Depression_2060           =                                  (1-
Opioid_in_Effect_Site_1010^Gamma_2075/(C50_2074^Gamma_2075+
Opioid_in_Effect_Site_1010^Gamma_2075) )*(Brain_CO2_2040/Base-
line_CO2_2071)^F_2076
```

(b) Output of Model when Run with Ventilatory Depression Model and Sedation Model Enabled The same simulation (Formulation In Inhaler 3020=5 milliliters at time=0) was run in the two opioid model as illustrated in Example 3(a) and FIGS. 13A, 13B and 13C. FIG. 14 shows the time course of Formulation In Inhaler 3020 (Line 1), Formulation In Lung (Rapid Opioid) 3040 (Line 2), and Formulation In Lung (Slow Opioid) 3040 (Line 3), in the presence of ventilatory depression and sedation. The simulation showed that, over 12 minutes of run, the drug was inhaled by the patient. The rate of fall in the amount of drug in the inhaler was not perfectly linear, reflecting the slowed breathing with opioid-induced ventilatory depression. After approximately 12 minutes, the patient stopped inhaling more opioid, reflecting opioid-induced sedation. The rapidly acting opioid was quickly taken up into the systemic circulation, which limited how much accumulated in the lung, and produced a quick drop in concentration in the lung when the patient stopped inhaling more opioid. The slowly acting opioid was taken up slowly by the lung, which permitted more drug to accumulate in the lung during inhalation, and the administration of opioid into the systemic circulation for over two hours following the end of opioid delivery to the patient.

FIG. 15 shows different variables for the same simulation. In FIG. 15, line 1 indicates the rapidly acting opioid concentration in the effect site (Rapid Drug Effect Site), over time, and demonstrates the rapid rise owing to quick absorption and rapid plasma-effect site equilibration, and a rapid drop owing to rapid metabolism. Line 2 is the slowly acting opioid concentration in the effect site (Slow Drug Effect Site), over time, and demonstrated a slow rise in concentration owing to slow absorption and slow plasma-effect site equilibration, and a slow decrease over time owing to slow metabolism. Line 3 shows the combined concentration of rapid and slow onset drug (Combined Opioid Effect Site Concentration) As can be seen, the combination reaches a peak during the administration of the first opioid.

FIG. 15 and FIG. 14 show different variables for the same simulation run, on the same X axis (time). One can therefore refer back to FIG. 14 to see that the patient stopped self-administering drug at approximately 12 minutes. When FIG. 14 is interposed with FIG. 15, we can see that this reflected the patients' response to the rapidly acting opioid, as the concentration of the slowly acting opioid was negligible at 12 minutes. However, the overall opioid concentration remained fairly steady over time. This reflected the slowly acting opioid gradually replacing the rapid acting opioid in Opioid In The Effect Site as the rapidly acting opioid was eliminated from the system through Rapid Drug Clearance.

FIG. 16 shows the time course of Ventilatory Depression 2060 during and after delivery of opioids with the two-opioid delivery system, in the same simulation run. FIG. 16 illustrates an initial decrease in ventilation to approximately 60% of baseline. As mentioned previously (in the description for FIG. 11), this is well tolerated by patients. As the CO2 builds up, ventilation was stimulated. Note that there was very little decrease in ventilation after this initial drop. The reason is that there is now adequate CO2 accumulation in the patient to continue driving ventilation.

As demonstrated by FIGS. 13A, 13B, 13C, 14, and 15, in the two drug embodiment of the device, the first drug acts as a 'probe' of the patient's sensitivity to opioids, and limits the dose of both the first and the second opioid. In this manner, the patient can receive an slowly acting opioid without receiving an excessive dose. A combination of two opioids, one of them fast acting, can therefore be used to increase the safety profile of either opioid alone, or, more particularly, of the slow acting opioid.

Example 4

Alfentanil and Morphine as Examples of Opioids in the Two Drug Model

This example shows an application of Example 3 to two specific drugs, namely, alfentanil and morphine, wherein alfentanil is the rapidly acting opioid and morphine is the slowly acting opioid.

FIGS. 17A, 17B and 17C, together, encompass: a Device Model 17010, comprising 2 Device Model 5010's, as described in FIGS. 5A and 5B and explained in Example 1, and each running in parallel, but each modified and re-labeled for the specific known parameters of the opioids alfentanil and morphine (shown in FIGS. 17A and 17B); a Ventilatory Depression Model 5030, as described in FIG. 2, a Sedation Model 5040, as described in FIG. 1, and a Two Drug Model, 17050, as described in FIG. 12 but re-labeled to reflect the specific drugs alfentanil and morphine (shown in FIG. 17C). FIGS. 17A, 17B and 17C expose all of the parameters 2070 of the ventilatory depression model, 17030. The parameters 4080 of the pharmacokinetic models for morphine and alfentanil, 17020, are now fully exposed. Alfentanil and morphine are each represented by a 3 compartment mammillary model with an effect site.

The model shown in FIGS. 17A, 17B and 17C can also be described by the following mathematical model, as represented in the Stella programming language. The constants for alfentanil and morphine are based on existing literature for these drugs.

```
Alfentanil_in_Inhaler(t) = Alfentanil_in_Inhaler(t − dt)      +
(− Inhale_Alfentanil) * dt
INIT Alfentanil_in_Inhaler   =   Alfentanil_Dose_ug
OUTFLOWS:
Inhale_Alfentanil   =   If Sedation_State   =   0   then
Alfentanil_Dose___ug/Dose_Duration*Ventilatory_Depression
else 0
Alfentanil_in_Lung(t)   =   Alfentanil_in_Lung(t   −   dt)      +
(Inhale_Alfentanil − Alfentanil_Uptake) * dt
INIT Alfentanil_in_Lung = 0
INFLOWS:
Inhale_Alfentanil   =   If Sedation_State   =   0   then
Alfentanil_Dose_ug/Dose_Duration*Ventilatory_Depression
else 0
OUTFLOWS:
Alfentanil_Uptake                                              =
Alfentanil_in_Lung*.693/Alfentanil_Absorption_Half_Life
Alfentanil_X1(t) = Alfentanil_X1(t − dt) + (Alfentanil_Cl2
+ Alfentanil_Cl3 + Alfentanil_CLe + Alfentanil_Uptake         −
Alfentanil_Cl1) * dt
INIT Alfentanil_X1 = 0
INFLOWS:
Alfentanil_Cl2   =   Alfentanil_X2*Alfentanil_K21             −
Alfentanil_X1*Alfentanil_K12
Alfentanil_Cl3   =   Alfentanil_X3*Alfentanil_K31             −
Alfentanil_X1*Alfentanil_K13
Alfentanil_CLe   =   Alfentanil_Xeffect*Alfentanil_Ke0        −
Alfentanil_X1*Alfentanil_Ke0*.001/Alfentanil_V1
```

-continued

```
Alfentanil_Uptake                                              =
Alfentanil_in_Lung*.693/Alfentanil_Absorption_Half_Life
OUTFLOWS:
Alfentanil_Cl1 = Alfentanil_X1*Alfentanil_K10
Alfentanil_X2(t)  =  Alfentanil_X2(t  –  dt)  +              (–
Alfentanil_Cl2) * dt
INIT Alfentanil_X2 = 0
OUTFLOWS:
Alfentanil_Cl2  =  Alfentanil_X2*Alfentanil_K21–
Alfentanil_X1*Alfentanil_K12
Alfentanil_X3(t)  =  Alfentanil_X3(t  –  dt)+                (–
Alfentanil_Cl3) * dt
INIT Alfentanil_X3 = 0
OUTFLOWS:
Alfentanil_Cl3  =  Alfentanil_X3*Alfentanil_K31–
Alfentanil_X1*Alfentanil_K13
Alfentanil_Xeffect(t) = Alfentanil_Xeffect(t – dt) +         (–
Alfentanil_CLe) * dt
INIT Alfentanil_Xeffect = 0
OUTFLOWS:
Alfentanil_CLe  =  Alfentanil_Xeffect*Alfentanil_Ke0         –
Alfentanil_X1*Alfentanil_Ke0*.001/Alfentanil_V1
Morphine_in_Inhaler(t) = Morphine_in_Inhaler(t – dt) +       (–
Inhale_Morphine) * dt
INIT Morphine_in_Inhaler = Morphine_Dose_mg*1000
OUTFLOWS:
Inhale_Morphine  =  If sedation_state  =  0  then
Morphine_Dose_mg*1000/Dose_Duration*Ventilatory_Depression
else 0
Morphine_in_Lung(t)  =  Morphine_in_Lung(t  –  dt)  +        +
(Inhale_Morphine –Morphine_Uptake) * dt
INIT Morphine_in_Lung = 0
INFLOWS:
Inhale_Morphine  =  If sedation_state  =  0  then
Morphine_Dose_mg*1000/Dose_Duration*Ventilatory_Depression
else 0
OUTFLOWS:
Morphine_Uptake                                              =
Morphine_in_Lung*.693/Morphine_Absorption_Half_Life
Morphine_X1(t) = Morphine_X1(t – dt) + (Morphine_Cl2         +
Morphine_Cl3  +  Morphine_CLe  +  Morphine_Uptake            –
Morphine_Cl1) * dt
INIT Morphine_X1 = 0
INFLOWS:
Morphine_Cl2  =  Morphine_X2*Morphine_K21                    –
Morphine_X1*Morphine_K12
Morphine_Cl3  =  Morphine_X3*Morphine_K31                    –
Morphine_X1*Morphine_K13
Morphine_CLe  =  Morphine_Xeffect*Morphine_Ke0               –
Morphine_X1*Morphine_Ke0*.001/Morphine_V1
Morphine_Uptake                                              =
Morphine_in_Lung*.693/Morphine_Absorption_Half_Life
OUTFLOWS:
Morphine_Cl1 = Morphine_X1*Morphine_K10
Morphine_X2(t) = Morphine_X2(t – dt) + (– Morphine_Cl2)      *
dt
INIT Morphine_X2 = 0
OUTFLOWS:
Morphine_Cl2  =  Morphine_X2*Morphine_K21                    –
Morphine_X1*Morphine_K12
Morphine_X3(t) = Morphine_X3(t – dt) + (– Morphine_Cl3)      *
dt
INIT Morphine_X3 = 0
OUTFLOWS:
Morphine_Cl3  =  Morphine_X3*Morphine_K31                    –
Morphine_X1*Morphine_K13
Morphine_Xeffect(t) = Morphine_Xeffect(t  –  dt) +           (–
Morphine_CLe) * dt
INIT Morphine_Xeffect = 0
OUTFLOWS:
Morphine_CLe  =  Morphine_Xeffect*Morphine_Ke0               –
Morphine_X1*Morphine_Ke0*.001/Morphine_V1
PaCO2(t) = PaCO2(t – dt) + (CO2_Accumulation – CO2Equilb)    *
dt
INIT PaCO2 = PaCO2@0
INFLOWS:
```

-continued

```
CO2_Accumulation   =   KelCO2*PaCO2@0 -
KelCO2*Ventilatory_Depression*PaCO2
OUTFLOWS:
CO2Equilb = ke0CO2*(PaCO2−PeCO2)
PeCO2(t) = PeCO2(t − dt) + (CO2Equilb) * dt
INIT PeCO2 = PaCO2@0
INFLOWS:
CO2Equilb = ke0CO2*(PaCO2−PeCO2)
Sedation_State(t) = Sedation_State(t  −  dt)                         +
(Sedation_Evaluator) * dt
INIT Sedation_State = 0
INFLOWS:
Sedation_Evaluator       =                                            if
Combined_Opioid_Effeci_Site_Concentration<Sedation_Threshold
then 0 else 1
Alfentanil_Absorption_Half_Life = 1
Alfentanil_Ce = Alfentanil_Xeffect/.001
Alfentanil_Cp = Alfentanil_X1/Alfentanil_V1
Alfentanil_Dose_ug = 1500
Alfentanil_K10 = 0.090957
Alfentanil_K12 = 0.655935
Alfentanil_K13 = 0.112828
Alfentanil_K21 = 0.214
Alfentanil_K31 = 0.017
Alfentanil_Ke0 = 0.77
Alfentanil_V1 = 2.18
C50 = 1.1
Combined_Opioid_Effeci_Site_Concentration                            =
Alfentanil_Ce/60+Morphine_Ce/70
Dose_Duration = 12
F = 4
Gamma = 1.2
ke0CO2 = 0.92
KelCO2 = 0.082
Morphine_Absorption_Half_Life = 2
Morphine_Ce = Morphine_Xeffect/.001
Morphine_Cp = Morphine_X1/Morphine_V1
Morphine_Dose_mg = 20
Morphine_K10 = 0.070505618
Morphine_K12 = 0.127340824
Morphine_K13 = 0.018258427
Morphine_K21 = 0.025964108
Morphine_K31 = 0.001633166
Morphine_Ke0 = 0.005
Morphine_V1 = 17.8
PaCO2@0 = 40
Sedation_Threshold = 1.5
Ventilatory_Depression         =                                    (1−
Combined_Opioid_Effeci_Site_Concentration^Gamma/ (C50^Gamma+
Combined_Opioid_Effeci_Site_Concentration^Gamma) )*(PeCO2/Pa
CO2@0)^F
```

The simulation was run with a starting parameter of 700 mcg of bioavailable alfentanil and 67 mcg of bioavailable morphine in the inhaler at time 0 (Alfentanil In Inhaler=700 mcg at time=0; Morphine In Inhaler=67 mcg at time 0). FIG. 18 and 19 shows the concentrations of various parameters when the simulation was run. FIG. 18 showed concentration of alfentanil (in ng/ml, line 1), morphine (in ng/ml, line 2) and combined opioid (in ng/ml of fentanyl equivalents, line 3) over time (in minutes) at the effect site following inhalation of the combined product. In this example, drug administration has terminated after 90% of the inhaled drug was delivered because of patient sedation. As can be seen, the alfentanil concentration rises quickly in the effect site (line 1) producing a rapid drug effect. The morphine drug effect rises quite slowly in the effect site (line 2), producing a slowly rising drug effect. Line 3 is shows the combined opioid effect site concentrations, where each drug has been adjusted for its potency relative to fentanyl. All three lines have different Y scales, as can be seen on the Y axis, to normalize the effect site concentrations for relative potency. As can be seen in line 3, the highest opioid exposure occurs at the time of inhalation, and is almost entirely due to-the alfentanil. However, as the alfentanil washes out of the effect site, it is almost exactly replaced by the influx of morphine into the effect site. A concentration at the site of effect of less than 25 ng/ml on the alfentanil scale (equivalent to 37.5 ng/ml on the morphine scale and 0.5 ng/ml on the fentanyl scale due to their relative potency) is considered sub-therapeutic; a patient will typically feel analgesic effects between 50 ng/ml and 100 ng/ml (on the alfentanil scale), side effects between 75 and 125 ng/ml (on the alfentanil scale) and toxic effects above 125 ng/ml (on the alfentanil scale).

FIG. 19 showed the ventilatory depression from the inhalation of an alfentanil morphine combination opioid delivery system. As shown in FIG. 19, the ventilation decreases to about 65% of baseline during drug administration, and then recovers to approximately 80% of baseline as CO2 accumulates. Ventilation is maintained at 80% of baseline throughout the next 4 hours, as the morphine effect is sustained.

As demonstrated in FIGS. 17A, 17B, 17C, 18, and 19, in the alfentanil morphine combination opioid delivery system, based on simulations using parameter values taken from the literature, the patient self-limiting opioid delivery system prevents administration of a toxic dose of opioid, and provides for the safe delivery of a slowly acting opioid by combining the slowly acting opioid with a rapidly acting opioid, and using the effects of the rapidly acting opioid to limit the total opioid exposure.

Example 5

Clinical Testing of Fentanyl Preparations in Human Subjects (a) Method of Preparation of Free and Liposome Encapsulated Fentanyl Preparations.

Preparations containing a mixture of free fentanyl and liposome encapsulated fentanyl were prepared by mixing an ethanolic phase with an aqueous phase. The ethanolic phase comprised ethanol, fentanyl citrate, phosphatidylcholine and cholesterol. The aqueous phase comprised water for injection. Before mixing, both phases were heated to a temperature of about 56 to 60 degrees centigrade. The two phases were mixed and the mixture was stirred for a further 10 minutes at 56-60 degrees centigrade. The mixture was then allowed to cool to room temperature over approximately two hours. Typically, each ml of the final aqueous formulation contained 500 mcg fentanyl (as 800 mcg of fentanyl citrate), 40 mg phosphatidylcholine, 4 mg cholesterol, and 100 mg ethanol, in a solution of water for injection. After filling, preparations were autoclaved for final sterilization. Final preparations contained between 35 to 45% of the fentanyl as free drug with the remainder in the encapsulated fraction.

(b) Treatment Protocol

The procedure of the following example shows how the administration of a mixture of free and liposome encapsulated fentanyl through the lungs of a patient delivers therapeutically effective concentrations to the bloodstream and that side effects of hypoxia are generally (but not always) preceded by somnolence, dizziness or sedation during the administration period.

Healthy volunteer subjects were treated with single or multiple doses of a mixture of free and liposome encapsulated fentanyl using the AEROECLIPSE® Nebulizer breath-actuated unit with compressed air set at 8 litres/minute. During each dosing period the nebulizer was charged with a 3 ml of the mixture of free (40%) and liposome encapsulated (60%) fentanyl and the subjects were instructed to inhale nebulized drug until the device no longer generated aerosol for inhalation. Subjects that become drowsy, sleepy or dizzy during the inhalation period were encouraged to continue to self-administer the drug until the nebulizer was no longer generated aerosol. Plasma samples were collected through the administration period and for the 12 hours following initiation of administration to monitor plasma fentanyl concentrations. Patients were monitored for any adverse events, including changes in respiratory rate and hypoxia.

Control subjects were given intravenous fentanyl.

(c) Measurement of Maximum Plasma Concentration and End of Dose Plasma Concentration In order to determine whether subjects could prevent toxic levels of drug by self-limiting the drug before a toxic effect was exhibited, maximum plasma concentration (Cmax) was plotted against plasma concentration at end of dosing (Ceod) (FIG. 20A). Ceod was found in most cases to be within 80% of Cmax, indicating that the maximum concentration of opioid was not significantly higher than the concentration at the time the subject stopped taking the opioid. This is in stark contrast to the control subjects (FIG. 20B) where subjects given intravenous fentanyl exhibited Cmax concentrations significantly higher than Ceod. This indicates an increased safety in titration of drug by the subjects, since the concentration (and resulting toxic effects) of the opioid will not increase significantly after the subject stops taking the opioid. This indicates that, in an inhaled opioid formulation of the disclosed concentration over a relatively long period of time (2-20 minutes), if the "end of dose" amount is non-toxic, the maximum concentration of opioid taken by the subject is likely also non-toxic.

(d) Determination of Time Points for Side Effects and Toxic Effects

In order for subjects to effectively self-titrate, side effects of the drug such as drowsiness, dizziness or ventilatory depression should occur before the onset of toxic effects. Toxic effects were defined in this experiment as blood hypoxia resulting in a blood oxygen saturation lower than 90% of normal for the subject. In order to determine whether side effects occur before toxic effects, time to a side effect, and time to a toxic effect, were plotted against time to end of dose (FIG. 21). For any end of dose time, time to side effect was equal or shorter than time to toxic effect, indicating that drowsiness, dizziness or ventilatory depression always took place before or at the time of toxic effect.

(e) Determination of Correlation Between Toxic Effect and Side Effect

In order for subjects to effectively self-titrate, a toxic effect should be almost always preceded by a side effect causing (or signaling) the cessation of administration of drug. FIG. 22 shows, for the total population of the study, that side effect is closely correlated to toxic effect, indicating that it is extremely likely that a subject exhibiting a toxic effect will have also exhibited a side effect.

This example shows, in a controlled trial of human subjects, that (1) a toxic effect is almost always preceded by a side effect, and that (2) Cmax of inhaled opioid, in the dose profile given in this example, is approximately Ceod. Therefore, a subject who stops administration of opioid when a side effect is felt will likely not reach opioid concentration levels required for toxic effect.

Example 6

Testing Various Nebulizer Technologies for Optimum Delivery of Drug

FIGS. 3, 5, 13 and 17 include a description of device models that are dependent on the rate of inhalation and the amount of drug delivered to the lung over a period of time. The ventilatory depression models in FIGS. 5, 13 and 17 predict how the side effects will limit the inhalation rate. In addition, there is a need to balance rate of opioid deposition on the lung with the rate of onset of effect at the site of action. The amount of drug dispensed with each inhalation must be controlled to below a selected threshold such that the drug formulation is conveniently, safely and effectively administered over a 4-20 minute period. To assist with the optimization of formulation and device selection, the performance of a device with a particular formulation can be characterized in vitro. The following example illustrates the testing of nebulizer technologies for optimum delivery of drug to the lungs.

Preparations containing a mixture of free fentanyl and liposome encapsulated fentanyl were prepared using the method described in Example 5. Final preparations contained between 35 to 45% of the fentanyl as free drug with the remainder in the encapsulated fraction.

The Andersen Cascade Impactor (ACI) technique is a well established method for characterization of the aerosol emitted from a nebulizer. (USP 26-NF21-2003, Chapter 601: Physical tests and determinations: aerosols. United States Pharmacopoeia, Rockville, Md., 2105-2123. United States Federal Drug Administration. 1998. Draft guidance: metered dose inhaler (MDI) and dry powder inhaler (DPI) drug products chemistry, manufacturing and controls documentation, Docket 98D-0997. United States Federal Drug Administration, Rockville, Md. Mitchell, JP; PA Costa; S Waters. 1987. An assessment of an Andersen Mark-II Cascade Impactor. J. Aerosol Sci. 19:213-221). A variety of parameters, including the rate of opioid output, the MMAD and the fine particle fraction, can be determined with this technique. The ACI was operated at 28.3 litres/min at ambient laboratory conditions to test commercially available nebulizers with the formation. The MMAD was calculated as per US Food and Drug Administration protocol 601 (USP 26-NF21-2003, Chapter 601: Physical Tests and Determinations: Aerosols. United States Pharmacopoeia, Rockville, Md., 2105-2123. United States Federal Drug Administration (FDA).) and the fine particle dose was determined as the fraction of the total aerosol output that was collected in the ACI that deposited on plates with cutoff parameters less than 4.7 microns. The amount of total opioid drug and lipid carrier deposited on the different stages of the ACI was determined by HPLC analysis.

Various commercially available small volume nebulizers, the breath-actuated AeroEclipse (Trudell Medical, London, Ontario), the breath-enhanced Pari-LC Plus (PARI GmbH, Starnberg, Germany), and two conventional small volume nebulizers, the MistyNeb (Allegiance Healthcare Corp., McGraw Park, Ill.) and the OptiMist (Maersk Medical Inc., McAllen, Tex.) were tested with the ACI technique. For each device, the theoretical rate of deposition of fentanyl in the lung was calculated using the experimentally determined opioid output rate (mcg/sec), multiplied by the average time (20 seconds) of inhalation over one minute and corrected for the experimentally determined fine particle fraction.

Healthy volunteer subjects were treated with single doses of a mixture of free and liposome encapsulated fentanyl (as described in above) using the various nebulizers (as described above), to determine whether the theoretical fentanyl deposited to the deep lung could be correlated to the average rate of delivery of total fentanyl in vivo. A summary of the results are shown below:

| Device | Theoretical Deposition (ACI) | Actual Deposition (in vivo) |
|---|---|---|
| a) AeroEclipse | 31 mcg/min | 29 mcg/min |
| b) MistyNeb | 23 mcg/min | 17 mcg/min |
| c) OptiMist | 26 mcg/min | 12 mcg/min |
| d) PariLC | 42 mcg/min | 37 mcg/min |

This experiment shows that the rate of inhalation with a specific fentanyl composition (as described in Example 5) yields a range of rates of deposition of fentanyl to the deep lung. Very good correlation between theoretical and actual deposition rates was realized with the breath-actuated AEROECLIPSE® nebulizer and the breath-enhanced PARILC® Plus Nebulizer. Poor correlation between theoretical and actual was observed for the conventional small volume jet nebulizers, MISTNEB® nebulizer and OPTIMIST® nebulizer, with actual in vivo deposition lower than predicted by the in vitro studies. The experiment also shows that other combinations of composition (with different concentration of opioid or different opioid ratio), combined with a different nebulizer may be developed to yield a desired rate of deposition of opioid, and describes a method of determining optimal combinations using routine experimentation.

Example 7

Clinical Testing of Qualitative Effects of Fentanyl Preparations in Human Subjects The following example shows how the analgesic effects and side effects of an appropriate inhaled drug formulation can be used by patients to deliver therapeutically effective amount of analgesic.

Preparations containing a mixture of free fentanyl and liposome encapsulated fentanyl were prepared using the method described in Example 5. Final preparations contained between 35 to 45% of the fentanyl as free drug with the remainder in the encapsulated fraction.

Post-surgical patients undergoing arthroscopic anterior cruciate ligament repair were studied. A standardized general anesthetic was administered with intravenous fentanyl as the intra-operative opioid analgesic. Following the surgery, with the patients recovering in the Post Anesthetic Care Unit (PACU), the patients were treated with a mixture of free and liposome encapsulated fentanyl using the AeroEclipse™ Nebulizer breath-actuated unit with compressed air set at 8 litres/minute when they first indicated that they were experiencing moderate or severe pain. The patients self-regulated their dosing by voluntary inhalations from the mouth-piece of the AeroEclipse nebulizer charged with 3 ml of the mixture of free and liposome encapsulated fentanyl. Patients were instructed to report the time of onset of first perceptible analgesia and stop the self-administration at onset of effective pain or the onset of side effects. Subjects not achieving effective analgesia at the point the nebulizer was no longer generating aerosol were provided a second nebulizer charged with an additional 3 ml of the mixture of free and liposome encapsulated fentanyl. In this manner, patients were, in effect, given treatment "ad libitum". Patient self-administration of the nebulized drug involved the patient grasping the nebulizer with their hand or hands, placing the mouth piece of the nebulizer in their mouth with a tight seal, and activating the nebulizer during the inspiration period of a breathing cycle. Patients were instructed to "breathe normally" throughout the treatment until they reached analgesia.

Patients were monitored for any adverse events, including changes in respiratory rate and hypoxia. Patients were also asked to describe their level of pain as "none", "mild", "moderate", or "severe", before and after self-administration of the nebulized drug, as well as at the time of first experience of breakthrough pain.

During this "single dose" or "single treatment period" study, a conventional analgesic medication (intravenous morphine) was available to all patients at any time they experienced breakthrough pain.

Most of the post-surgical patients (80%) were eligible for treatment with the nebulized drug and reported "moderate" (46%) to "severe" (34%) post-operative pain in the PACU. Patients reporting only "mild" post-operative pain were not treated.

95% of the treatment eligible patients successfully used the study drug to rapidly achieve perceptible analgesia soon after commencing nebulization, and were able to self-titrate their dosing to the point of adequate/effective analgesia via stopping the nebulization. The mean time to first perceptible analgesic effect was 5.2 minutes. The average time to effective analgesia was 22.8 minutes of self-administration of drug. At adequate/effective analgesia, 5% reported no pain, 78% reported "mild" pain, and 12% reported their pain subsided from "severe" to "moderate". Patients that achieved adequate/effective analgesia were monitored for breakthrough pain. 17% of the patients required no further opioid during the 12 hour study period. Breakthrough pain was experienced on average more than 2 hours after completion of inhalation by 83% of the patients and required administration of intravenous morphine.

Of the patients treated, 95% reported effective analgesia after self-administration of the nebulized drug, and none experienced toxic effects. 84% of the patients stopped self-administration of drug when they reached a satisfactory level of analgesia. 11% of patients stopped self-administration of drug shortly (3 minutes) after feeling (and reporting) a side effect (sleepiness or nausea).

These results show that the analgesic effects and side effects of an appropriate inhaled drug formulation can be used by patients to deliver therapeutically effective amount of analgesic, while avoiding toxic effects.

Example 8

Testing Various Formulations for Optimum Delivery of Drug

The following example shows various opioid formulations appropriate for use in the invention. The formulations are based on the known pharmacokinetic and pharmacodynamic profiles of the component drugs, their known equivalent potency as compared to fentanyl, and the outcomes of the clinical studies described above.

Preparations containing a mixture of opioids are prepared according to the formulation chart shown below:

| Rapid onset opioid | | Sustained Effect Opioid | | Rate of Deposition |
| --- | --- | --- | --- | --- |
| Type | Concentration (mcg/ml) | Type | Concentration (mcg/ml) | In the Lung (mcg/min) |
| Fentanyl | 200 | Liposomal fentanyl | 300 | 15-60 |
| Fentanyl | 175 | Liposomal fentanyl | 325 | 15-60 |
| Fentanyl | 125 | Liposomal fentanyl | 275 | 15-60 |
| Alfentanil | 1600 | Morphine | 12000 | 400-1600 |
| Alfentanil | 1400 | Morphine | 13000 | 400-1700 |
| Alfentanil | 1800 | Morphine | 11000 | 400-1500 |

The foregoing description is by way of example only and shall not be construed to limit the scope of the invention as defined by the following claims.

The invention claimed is:

1. A pain management method enabling a pain sufferer to self medicate by repeated dosing with an opioid formulation to achieve analgesia while avoiding toxicity, wherein the method relies solely on the actions of the pain sufferer to manage intake of said opioid during the medication process, said method comprising the steps of:
the pain sufferer continuously inhaling the formulation using a pulmonary drug delivery device adapted to deliver particles of the formulation into the lungs at an effective rate to produce analgesia; and
stopping inhalation when, during the medication process, satisfactory analgesia is achieved or at the onset of a side effect;
wherein the formulation comprises an effective amount of fentanyl and liposomally encapsulated fentanyl; the combination and a concentration of each opioid, and an effective rate of delivery of the particles selected so that, during inhalation, analgesia is achieved before the onset of said side effect, and the onset of said side effect occurs before the onset of toxicity, and so that the maximum total opioid plasma concentration does not reach toxic levels, whereby the onset of said side effect can be used by the pain sufferer to terminate inhalation to avoid toxicity by said stopping of inhalation of said formulation by the pain sufferer when said onset of said side effect is felt by the pain sufferer, wherein the ratio of said fentanyl to said liposomally encapsulated fentanyl is selected such that a combined pharmacokinetic profile of the fentanyl and the liposomally encapsulated fentanyl has a combined effect curve providing a peak concentration at an effect site at between 10 and 30 minutes and a concentration at the effect site of a magnitude of at least 85% of said peak concentration for at least two hours.

2. The method of claim 1 wherein the formulation is dispensed by the pulmonary drug delivery device at a mass median aerodynamic diameter of from 1 to 5 microns.

3. The method of claim 1 wherein the concentration and type of each opioid is selected so that the maximum total opioid plasma concentration at the onset of side effect is no less than 66% of the maximum opioid plasma concentration.

4. The method of claim 1 wherein the ratio of concentration of free fentanyl to liposomally encapsulated fentanyl is from 1:5 to 2:1.

5. The method of claim 1 wherein the total opioid concentration is from 250 to 1500 mcg/ml, the free fentanyl concentration is from 100 to 400 mcg/ml mcg/ml and the liposomally encapsulated fentanyl concentration is from 250 to 750 mcg/ml.

6. The method of claim 1 wherein from 4 to 50 mcg/min. of free fentanyl and 5 to 150 mcg/min of liposomally encapsulated fentanyl is deposited in the lungs during inhalation.

7. The method of claim 1 wherein the administration takes place over between 50 and 500 inhalations.

8. A pulmonary drug delivery device for use in the pain management method of claim 1, said device comprising:
a container containing an opioid formulation;
an outlet coupled to the container;
said opioid formulation comprising an effective amount of a combination of fentanyl and liposomally encapsulated fentanyl;
a nebulizer or aerosolizer coupled to the container for dispensing particles of said formulation through said outlet and into the lungs through actuation by conscious pain sufferer effort and at an effective rate whereby, during inhalation, analgesia is achieved before the onset of an opioid side effect, and the onset of said side effect occurs before the onset of toxicity, and so that the maximum opioid plasma concentration does not reach toxic levels, and whereby the onset of said side effect can be used by the pain sufferer to terminate inhalation to avoid toxicity by a stopping of inhalation of said formulation by the pain sufferer when said onset of said side effect is felt by the pain sufferer, wherein the ratio of said fentanyl to said liposomally encapsulated fentanyl is selected such that a combined pharmacokinetic profile of the fentanyl and the liposomally encapsulated fentanyl has a combined effect curve providing a peak concentration at an effect site at between 10 and 30 minutes and a concentration at the effect site of a magnitude of at least 85% of said peak concentration for at least two hours.

9. A pulmonary drug delivery device for use in the pain management method of claim 1, said device comprising:
   a container containing an opioid formulation;
   an outlet coupled to the container;
   a nebulizer or aerosolizer coupled to the container for dispensing particles of said formulation through said outlet and into the lungs, said nebulizer or aerosolizer requiring conscious pain sufferer effort to be actuated;
   wherein said opioid formulation has a combination of opioids, a concentration of opioids, and an effective rate of delivery of the particles selected so that, during inhalation, analgesia is achieved before the onset of said side effect, and the onset of said side effect occurs before the onset of toxicity, and so that the maximum opioid plasma concentration does not reach toxic levels, whereby the onset of said side effect can be used by the pain sufferer to terminate inhalation to avoid toxicity, wherein the opioid formulation consists of fentanyl and liposomally encapsulated fentanyl, and wherein the ratio of said fentanyl to said liposomally encapsulated fentanyl is selected such that a combined pharmacokinetic profile of the fentanyl and the liposomally encapsulated fentanyl has a combined effect curve providing a peak concentration at an effect site at between 10 and 30 minutes and a concentration at the effect site of a magnitude of at least 85% of said peak concentration for at least two hours.

10. The device of claim 8 wherein said particles have a mass median aerodynamic diameter of from about 1 to 5 microns.

11. The device of claim 8 wherein said means dispenses between 0.2% to 1% of the formulation per inhalation.

12. The device of claim 8 wherein the concentration and type of each opioid is selected so that the maximum opioid plasma concentration at the onset of side effect is no less than 66% of the maximum opioid plasma concentration.

13. The device of claim 9 wherein the ratio of concentration of free fentanyl to liposomally encapsulated fentanyl is from 1:5 to 2:1.

14. The device of claim 9 wherein the total opioid concentration is from 250 to 1500 mcg/ml.

15. The device of claim 9 wherein the total opioid concentration is from 250 to 1500 mcg/ml, the free fentanyl concentration is from 100 to 400 mcg/ml and the liposomally encapsulated fentanyl concentration is from 250 to 1500 mcg/ml.

16. The device of claim 9 wherein 4 to 50 mcg/min. of free fentanyl and 5 to 150 mcg/min of liposomally encapsulated fentanyl is deposited in the lungs during inhalation.

* * * * *